(12) United States Patent
Meutermans et al.

(10) Patent No.: US 7,989,422 B2
(45) Date of Patent: Aug. 2, 2011

(54) ANTIBACTERIAL AGENTS

(75) Inventors: Wim Meutermans, Toowong (AU);
Declan McKeveney, Coorparoo (AU);
Johannes Zuegg, Wynnum (AU);
Rajaratnam Premraj, Eight Mile Plains (AU); Craig Muldoon, Springwood (AU); Giang Thanh Le, Mount Gravatt (AU)

(73) Assignee: Alchemia Limited, Eight Mile Plains (AU)

( * ) Notice: Subject to any disclaimer, the term of this patent is extended or adjusted under 35 U.S.C. 154(b) by 474 days.

(21) Appl. No.: 12/096,771

(22) PCT Filed: Dec. 20, 2006

(86) PCT No.: PCT/AU2006/001939
§ 371 (c)(1),
(2), (4) Date: Aug. 15, 2008

(87) PCT Pub. No.: WO2007/070947
PCT Pub. Date: Jun. 28, 2007

(65) Prior Publication Data
US 2009/0023669 A1    Jan. 22, 2009

(30) Foreign Application Priority Data
Dec. 22, 2005 (AU) ............... 2005907230

(51) Int. Cl.
*A61K 31/7052* (2006.01)
*A61K 31/7056* (2006.01)
*A61K 31/706* (2006.01)
*A61K 31/416* (2006.01)
*C07D 235/18* (2006.01)
*C07H 5/04* (2006.01)

(52) U.S. Cl. ............... 514/24; 514/25; 514/43; 514/395; 548/304.7; 536/17.3; 536/27.1; 536/22.1

(58) Field of Classification Search ............... None
See application file for complete search history.

(56) References Cited

U.S. PATENT DOCUMENTS
4,495,180 A * 1/1985 Alexander ............... 514/46
4,507,287 A * 3/1985 Dixon ............... 514/43
5,691,320 A * 11/1997 von Borstel et al. ........... 514/50

FOREIGN PATENT DOCUMENTS
| WO | WO-02/32915 A1 | 4/2002 |
| WO | WO-03/070715 A1 | 8/2003 |
| WO | WO-03/082846 A1 | 10/2003 |
| WO | WO-2004/014929 A1 | 2/2004 |
| WO | WO-2004/035062 A1 | 4/2004 |

OTHER PUBLICATIONS

Atkins et al., "The use of linezolid in the treatment of vancomycin-resistant *Enterococcal septicaemia* in two patients with burn injuries" Burns (2002) vol. 28 pp. 185-188.*
Lavrenov et al., "The Interaction of Per-O-Acetylated Acyclic 1-(1-Butylindol-3-yl)-1-deoxy-ketoses with Silylated Uracil" Nucleosides, Nucleotides, and Nucleic Acids (2004) vol. 23 No. 1&2, pp. 281-289.*
Oliveria et al., "A Very Simple Synthesis of 1-(Ethyl 6-O-Acetyl-2,3,4-trideoxya- D-erythro-hex-2-enopyranos-4-yl)-1,2,3-triazole Derivatives" Synthesis (2006) No. 3, pp. 0467-0470.*
International Search Report mailed Feb. 6, 2007, for PCT Application No. PCT/AU2006/001939 filed Dec. 20, 2006, four pages.
Ritter, T.K. et al. (2003). "Carbohydrate-Based Drug Discovery in the Battle Against Infections: New Opportunities Arising from Programmable One-Pot Oligosaccharide Synthesis" in *Carbohydrate-Based Drug Discovery*, Wong, C-H. ed., Weinheim: New York, NY, 2:899-932.

* cited by examiner

*Primary Examiner* — Eric S Olson
(74) *Attorney, Agent, or Firm* — Morrison & Foerster LLP

(57) ABSTRACT

The present invention, in one aspect, provides a method of inhibiting bacterial growth by contacting bacteria with an effective amount of at least one monosaccharide compound of formula (1) as described herein:

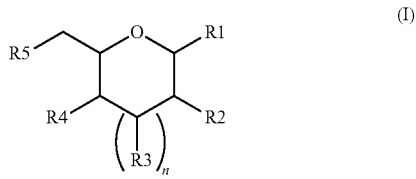

18 Claims, No Drawings

ANTIBACTERIAL AGENTS

CROSS-REFERENCE TO RELATED APPLICATIONS

This application is a National Phase application under 35 U.S.C. §371 of International Application No. PCT/AU2006/001939 filed Dec. 20, 2006 and claims the benefit of Australian Application No. 2005907230, filed Dec. 22, 2005, the disclosures of which are incorporated herein by reference in their entirety.

FIELD OF INVENTION

The present invention relates to novel carbohydrate compounds and method of inhibiting bacterial growth.

BACKGROUND

Since the introduction of penicillin over fifty years ago, there has been continuous growth in the number of antibiotics commercially available for treatment of bacterial infections. As a result, today there are about 350 drugs on the market used for the treatment of a wide range of bacterial infections. One of the problems of continued use of existing drugs is the ever increasing acquisition of resistance through mutation and exchange of genes (Ritter et al *Carbohydrate-Based Drug Discovery* (2003), 899-932). Often patients with bacterial infections cannot be treated adequately with the existing drugs, as many bacteria have developed multi-drug resistance. There is a great medical need for new antibacterials that are effective against the various multi-drug resistant bacteria. The Applicant has identified a number of new classes of compounds (PCT AU03/00384; PCT/AU2003/001008)). Several compounds described in these applications have now been shown to possess promising antimicrobial activity, including activity against MRSA (Methicillin-resistant *Staphylococcus aureus*) and VRE (vancomycin-resistant enterococci). In addition, several new chemotypes have been identified with potent antimicrobial activity. The applicant has also discovered disaccharides that have antibacterial properties (PCT/AU2003/01377). None of the new drugs in the art contain small molecules based on monosaccharide scaffolds as disclosed in these patents applications. WO 03/070715 discloses antimicrobial agents comprising glycofuranose compounds derived from hexose sugars which are different from the compounds of the present invention because the compounds of the present invention are either glycopyranose compounds of hexose sugars or glycofuranose compounds of pentose sugars.

SUMMARY OF THE INVENTION

It is an object of the present invention to provide novel compounds and new uses of various related compounds.

The present invention, in one aspect, provides a method of inhibiting bacterial growth by contacting bacteria with an effective amount of at least one monosaccharide compound of formula (1):

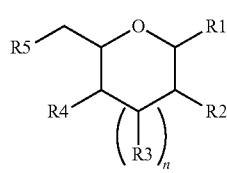

formula I

Wherein, n is 0 or 1; the ring may be of any configuration and the anomeric center may be of either the α or β configuration;

R1 is selected from the group consisting of hydrogen; OZ; SZ; OPO$_2$(OZ)Z; SO$_2$N(Z)Q; S(=O)N(Z)Q; N-Het wherein N and Het combine to form a heterocycle which may be further substituted with one or more U moieties; and —N(Z)Y wherein:

Y is selected from hydrogen, or the following, where G denotes the point of connection to the nitrogen atom in N(Y)Z;

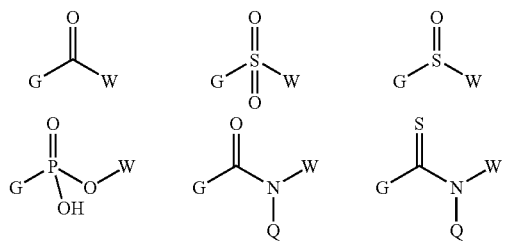

Q is selected from hydrogen or W;

the groups W are independently selected from alkyl, alkenyl, alkynyl, heteroalkyl, aryl, heteroaryl, arylalkyl or heteroarylalkyl of 1 to 20 carbon atoms which is optionally substituted, branched and/or linear. Typical substituents include but are not limited to OH, NO, NO$_2$, NH$_2$, N$_3$, halogen, CF$_3$, CHF$_2$, CH$_2$F, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid; the term heteroalkyl includes alkyl groups which incorporate one or more heteroatoms within the alkyl chain;

each occurrence of Z is independently selected from the group consisting of: hydrogen, alkyl, alkenyl, alkynyl, heteroalkyl, acyl, arylacyl, heteroarylaryl, aryl, heteroaryl, arylalkyl or heteroarylalkyl of 1 to 20 carbon atoms which is optionally substituted, branched and/or linear. Typical substituents include but are not limited to OH, NO, NO$_2$, NH$_2$, N$_3$, halogen, CF$_3$, CHF$_2$, CH$_2$F, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid; the term heteroalkyl includes alkyl groups which incorporate one or more heteroatoms within the alkyl chain; or wherein each occurrence of U is independently selected from the group consisting of: OH, NO, NO$_2$, NH$_2$, N$_3$, halogen, CF$_3$, CHF$_2$, CH$_2$F, nitrile, alkoxy, aryloxy, amidine, guanidinium, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid; heteroaryloxy, aminoaryl, aminoheteroaryl, thioalkyl, thioaryl, thioheteroaryl, alkyl, alkenyl, alkynyl, acyl, arylacyl, heteroarylaryl; of 1 to 20 carbon atoms which is optionally substituted, branched and/or linear.

The groups R2, R3, R4 and R5 are independently selected from OZ or N-Het wherein N and Het combine to form a heterocycle which may be further substituted with U groups; or N(Z)Y or OPO$_2$(OZ)Z, wherein the groups Z and Y are as defined above.

It is understood that the rules of molecular stoichiometry will be upheld by the default addition of hydrogen atoms as required.

In a preferred embodiment, the invention relates the method wherein the compound is selected from the group consisting of the gluco- or galacto- or allo-configuration.

In a preferred embodiment the invention relates to said method wherein at least one of R1-R5 is N-Het.

In a preferred embodiment the invention relates to a method wherein the heterocycle is a monocyclic or bicyclic ring of 4 to 10 membered ring structure.

In a preferred embodiment the invention relates to a method wherein the heterocyclic ring is selected from the group consisting of triazoles, benzimidazoles, benzimidazolothione, benzimidazolone, imidazole, hydanthione, thiohydanthione and purine.

In a preferred embodiment the invention relates to a method wherein any one of R2 and R4 is N-Het, wherein the heterocycle is a monocyclic or bicyclic ring of 4 to 10 membered ring structure.

In another aspect, the invention provides a compound of formula (1) wherein any one of R1-R5 is N-Het.

In a preferred embodiment, the invention relates to a compound of formula (1) wherein the heterocycle is a monocyclic or bicyclic ring of 4 to 10 membered ring structure.

In a preferred embodiment the invention relates to the compound of formula (1) wherein any one of R2 and R4 is N-Het, wherein the heterocycle is a monocyclic or bicyclic ring of 4 to 10 membered ring structure.

In a preferred embodiment, the invention relates the compound of formula (1) wherein the compound is selected from the group consisting of the gluco- or galacto- or allo-configuration.

In a preferred embodiment the invention relates to the compound of formula (1) wherein the heterocyclic ring is selected from the group consisting of triazoles, benzimidazoles, benzimidazolothione, benzimidazolone, imidazole, hydanthione, thiohydanthione and purine.

In a preferred embodiment, the heterocyclic ring may be further substituted with U groups; wherein each occurrence of U is independently selected from the group consisting of: OH, NO, NO$_2$, NH$_2$, N$_3$, halogen, CF$_3$, CHF$_2$, CH$_2$F, nitrile, alkoxy, aryloxy, amidine, guanidinium, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid; heteroaryloxy, aminoaryl, aminoheteroaryl, thioalkyl, thioaryl, thioheteroaryl, alkyl, alkenyl, alkynyl, acyl, arylacyl, heteroarylaryl; of 1 to 20 carbon atoms which is optionally substituted, branched and/or linear.

In a preferred embodiment, the heterocyclic ring may be further substituted with U groups selected from the group consisting of substituted alkyl, aryl, carboxyl and amino.

In a preferred embodiment, the U group is selected from the group consisting of OH, NO, NO$_2$, NH$_2$, N$_3$, halogen, CF$_3$, CHF$_2$, CH$_2$F, nitrile, alkoxy, aryloxy, amidine, guanidinium, carboxylic acid, carboxylic acid ester, carboxylic acid amide, aryl, cycloalkyl, heteroalkyl, heteroaryl, primary or secondary or tertiary amines, aminoacyl, carbonyl and substituted or unsubstituted imine. The term primary, secondary and tertiary amines includes alkyl and aryl amines.

In a preferred embodiment, each occurrence of Z is independently selected from the group consisting of: hydrogen, alkyl, alkenyl, alkynyl, heteroalkyl, acyl, arylacyl, heteroarylaryl, aryl, heteroaryl, arylalkyl or heteroarylalkyl of 1 to 20 carbon atoms which is optionally substituted, branched and/or linear.

In a preferred embodiment, the term "optionally substituted" or "optional substituents" include OH, NO, NO$_2$, NH$_2$, N$_3$, halogen, CF$_3$, CHF$_2$, CH$_2$F, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid; the term heteroalkyl includes alkyl groups which incorporate one or more heteroatoms within the alkyl chain.

In a preferred embodiment, the compound is selected from the group consisting of:

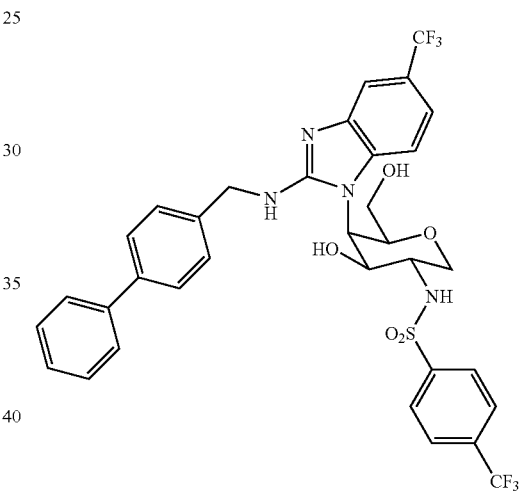

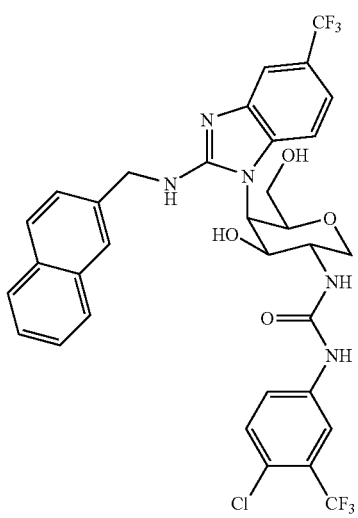

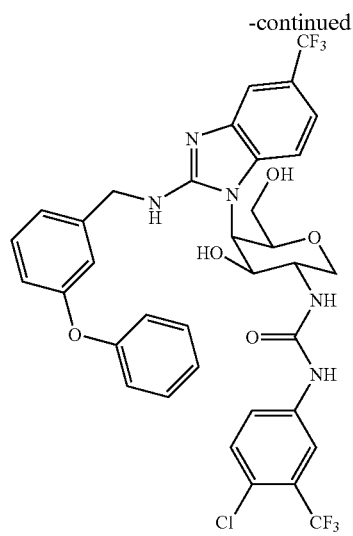

In another aspect, the invention provides a compound of formula (1) wherein R1 is silyloxy and R2, R3, R4 and R5 are as defined above. Typical silyloxy groups include tertiary-butyldiphenylsilyloxy, tertiary-butyldimethylsilyloxy and other similar alkyl and aryl silyloxy groups.

The term "halogen" denotes fluorine, chlorine, bromine or iodine, preferably fluorine, chlorine or bromine.

The term "alkyl" used either alone or in compound words such as "optionally substituted alkyl", "optionally substituted cycloalkyl", "arylalkyl" or "heteroarylalkyl", denotes straight chain, branched or cyclic alkyl, preferably C1-20 alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3 dimethylpentyl, 4,4-dimethylpentyl, 1,2-dimethylpentyl, 1,3-dimethylpentyl, 1,4-dimethylpentyl, 1,2,3trimethylbutyl, 1,1,2-trimethylbutyl, 1,1,3-trimethylbutyl, octyl, 6-methylheptyl, 1-methylheptyl, 1,1,3,3tetramethylbutyl, nonyl, 1-, 2-, 3-, 4-, 5-, 6- or 7-methyloctyl, 1-, 2-, 3-, 4- or 5-ethylheptyl, 1-, 2- or 3propylhexyl, decyl, 1-, 2-, 3-, 4-, 5-, 6-, 7- or 8-methylnonyl, 1-, 2-, 3-, 4-, 5- or 6-ethyloctyl, 1-, 2-, 3 or 4-propylheptyl, undecyl 1-, 2-, 3-, 4-, 5-, 6-, 7-, 8 or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2 pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkylene" used either alone or in compound words such as "optionally substituted alkylene" denotes the same groups as "alkyl" defined above except that an additional hydrogen has been removed to form a divalent radical. It will be understood that the optional substituent may be attached to or form part of the alkylene chain.

The term "alkenyl" used either alone or in compound words such as "optionally substituted alkenyl" denotes groups formed from straight chain, branched or cyclic alkenes including ethylenically mono-, di- or polyunsaturated alkyl or cycloalkyl groups as defined above, preferably C2-6 alkenyl. Examples of alkenyl include vinyl, allyl, 1-methylvinyl, butenyl, iso-butenyl, 3-methyl-2butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl; 1,4-pentadienyl, 1,3cyclopentadienyl, 1,3-hexadienyl, 1,4-hexadienyl, 1,3cyclohexadienyl, 1,4-cyclohexadienyl, 1,3-cycloheptadienyl, 1,3,5-cycloheptatrienyl and 1,3,5,7-cyclooctatetraenyl.

The term "alkynyl" used either alone or in compound words, such as "optionally substituted alkynyl" denotes groups formed from straight chain, branched, or mono- or poly- or cyclic alkynes, preferably C2-6 alkynyl.

Examples of alkynyl include ethynyl, 1-propynyl, 1- and 2butynyl, 2methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyne-3-yl, 7-dodecynyl, 9-dodecynyl, 10-dodecynyl, 3-methyl-1-dodecyn-3-yl, 2-tridecenyl, 11tridecenyl, 3-tetradecenyl, 7-hexadecenyl, 3-octadecenyl and the like.

The term "alkoxy" used either alone or in compound words such as "optionally substituted alkoxy" denotes straight chain or branched alkoxy, preferably C1-7 alkoxy. Examples of alkoxy include methoxy, ethoxy, propyloxy, isopropyloxy and the different butoxy isomers.

The term "aryloxy" used either alone or in compound words such as "optionally substituted aryloxy" denotes aromatic, heteroaromatic, arylalkoxy or heteroaryl alkoxy, preferably C6-13 aryloxy. Examples of aryloxy include phenoxy, benzyloxy, 1-naphthyloxy, and 2-naphthyloxy.

The term "acyl" used either alone or in compound words such as "optionally substituted acyl" or "heteroarylacyl" denotes carbamoyl, aliphatic acyl group and acyl group containing an aromatic ring, which is referred to as aromatic acyl or a heterocyclic ring which is referred to as heterocyclic acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, and icosanoyl; alkoxycarbonyl such as methoxycarbonyl, ethoxycarbonyl, t butoxycarbonyl, t-pentyloxycarbonyl and heptyloxycarbonyl; cycloalkylcarbonyl such as cyclopropylcarbonyl cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanol, phenylbutanoyl, phenylisobutyl, phenylpentanoyl and phenylhexanoyl) and naphthylalkanoyl (e.g. naphthylacetyl, naphthlpropanoyl and naphtliylbutanoyl); aralkenyl such as phenylalkenoyl (e.g. phenylpropenyl, phenylbutenoyl, phenylmethacrylyl, phenylpentanoyl and phenylhexanoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and naphthyloxycarbonyl, aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and naphthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienyglyoxyloyl.

The term "aryl" used either alone or in compound words such as "optionally substituted aryl", "arylalkyl" or "heteroaryl" denotes single, polynuclear, conjugated and fused residues of aromatic hydrocarbons or aromatic heterocyclic ring systems. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, pyrrolyl, furanyl, imidazolyl, pyrrolidinyl, pyridinyl, piperidinyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Preferably, the aromatic heterocyclic ring system contains 1 to 4 heteroatoms independently selected from N, O and S and containing up to 9 carbon atoms in the ring.

The term "heterocycle" used either alone or in compound words as "optionally substituted heterocycle" denotes monocyclic or polycyclic heterocyclyl groups containing at least one heteroatom atom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated to 3 to 6-membered heteromonocyclic groups containing 1 to 4 nitrogen atoms, such as, pyrrolidinyl, imidazolidinyl, piperidin or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered heteromonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoxazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as, thiazolyl or thiadiazolyl; saturated 3 to 6-membered heteromonocyclic group containing 1 to 2 sulphur atoms and 1 to 3 nitrogen atoms, such as thiazolidinyl; and unsaturated condensed heterocyclic group containing 1 to 2 sulphur atoms and 1 to 3 nitrogen atoms, such as, benzothiazolyl or benzothiadiazolyl.

In another form, the invention comprises a method of inhibiting bacterial growth in an animal or human comprising administering an effective amount of at least one monosaccharide compound of formula (1).

In another aspect, the invention provides for a pharmaceutical composition comprising at least one of the compounds described herein, or tautomers, esters, solvates, or pharmaceutically acceptable salts thereof, and a pharmaceutically acceptable carrier.

The bacterial may be Gram-positive or Gram-negative bacteria. The bacteria may comprise an *E. coli* bacteria, a Staphylococci Bacteria such as *Staphylococcus aureus*, or other bacteria such as *Micrococcus luteus* (ATCC272), *Staphylococcus aureus* (ATCC29213), *Staphylococcus aureus* (ATCC43300) MRSA, *Enterococcus faecalis* (ATCC29212), *Enterococcus faecalis* (ATCC51299) Vancomycin resistant and *Streptococcus pyogenes* (ATCC8668).

The method may comprise administering an effective amount of a compound of the first aspect, to a subject in need of such treatment. The subject may be a human, or may be a domestic, companion or zoo animal.

In another form, the invention may reside in an antibacterial composition comprising at least one compound as described above. The composition may comprise a pharmaceutical composition.

The compounds of the invention may be mixed with a pharmaceutical acceptable carrier, adjuvant, or vehicle, which may comprise a-toxic carrier, adjuvant, or vehicle that may be administered to a patient, together with a compound of this invention, and which does not destroy the pharmacological activity thereof.

The pharmaceutical derivative may comprise a salt, ester, salt of an ester or other derivative of a compound of this invention which, upon administration to a recipient, is capable of providing, either directly or indirectly, a compound of this invention, although no limitation is meant thereby.

Compounds of the invention may be administered orally such as by means of a tabled, powder, liquid, emulsion, dispersion and the like; by inhalation; topically such as by means of a cream, ointment, salve etc; and as a suppository, although no limitation is meant thereby.

The compounds of the invention may be administered together with one or more drugs, including antibacterial agents such as antibiotics, for the treatment of bacterial infections.

In another aspect, the invention provides a compound of formula (1) when used for the treatment of a disease.

In another aspect, the invention provides a pharmaceutical composition comprising a compound of formula (1) when used for the treatment of a disease.

Methods and pharmaceutical carriers for preparation of pharmaceutical compositions are well known in the art, as set out in textbooks such as Remington's Pharmaceutical Sciences, 19th Edition, Mack Publishing Company, Easton, Pa., USA.

It will be clearly understood that, if a prior art publication is referred to herein, this reference does not constitute an admission that the publication forms part of the common general knowledge in the art in Australia or in any other country.

DETAILED DESCRIPTION OF THE INVENTION

Various non-limiting embodiments of the invention will be described with reference to the following examples. Where appropriate, the following abbreviations are used.

Ac Acetyl
DTPM 5-Acyl-1,3-dimethylbarbiturate
DIPEA N,N-Diisopropylethylamine
Ph Phenyl
TBDMS t-Butyldimethylsilyl
TBDPS t-Butyldiphenylsilyl Bn benzyl
Bz benzoyl
Me methyl
DCE 1,2-dichloroethane
DCM dichloromethane, methylene chloride
Tf trifluoromethanesulfonyl
Ts 4-methylphenylsulfonyl, p-toluenesulfonyl
DMF N,N-dimethylformamide
DMAP N,N-dimethylaminopyridine
α, α-DMT α, α-dimethoxytoluene, benzaldehyde dimethyl acetal
DMSO dimethylsulfoxide
DTT dithiothreitol
DMTST Dimethyl(methylthio)sulphoniumtrifluoromethanesulphonate
TBAF tetra-n-butylammonium fluoride Generally applicable synthetic procedures A) Fmoc Removal The resins were washed with dry DMF then treated with 1.5 mL of a solution of 20% v/v piperidine in DMF. The resins were shaken for 1 h and then drained and washed with DMF. The procedure was then repeated with the resins being finally washed with DMF (×3), MeOH (×3) and DCM (×3).

B) Cleavage from Resin (and Removal of any Boc Groups on Side Chains)

Each resin was treated with a solution of 10% TFA, 20% Et$_3$SiH in dry DCM (1.5 ml) for 3 h, drained into a test tube and washed with DCM (2.0 ml), The samples were concentrated in vacuo on the RVC.

Each cleaved product was treated with a solution of saturated ammonia in methanol (1.0 ml) and left at room temperature for 2 h. The samples were again concentrated in vacuo on the RVC.

C) Acylation

Acylating mixtures were prepared by dissolving the requisite carboxylic acid (0.5 mM) in anhydrous DMF (0.5 mL) and treating this solution first with HBTU (0.5 mM) followed by DIPEA (0.5 mM). Following mixing, each solution was allowed to stand for 10 min. prior to addition of the resin bound substrate. The reaction mixture was shaken at room temperature overnight, filtered and washed with DMF (×3), MeOH (×1), DMF (×3), MeOH (×1) and DCM (×3).

D) Reduction of Azide

Equal volumes of a solution of 1,4-Dithio-DL-threitol (DTT, 0.2 M in DMF) and lithium tert-butoxide (0.2 M in DMF) were added to the resin bound substrate and the reaction mixture shaken at room temperature for 6 h. The resin was drained, washed with dry DMF (×3), dry THF (×3), dry MeOH (×3), dry DCM (×3) and dried in vacuo.

Synthetic Schemes

Synthetic schemes are given for two of the libraries synthesised as being representative of the general approach taken during monosaccharide synthesis. This is not exhaustive and variations on these approaches were used.

TG 24

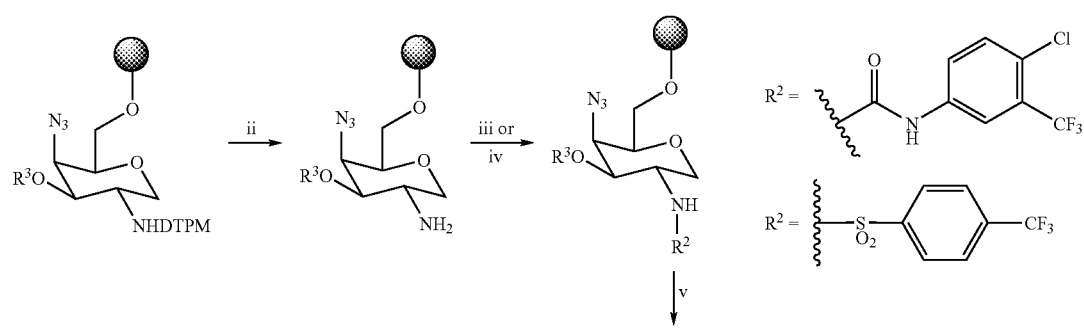

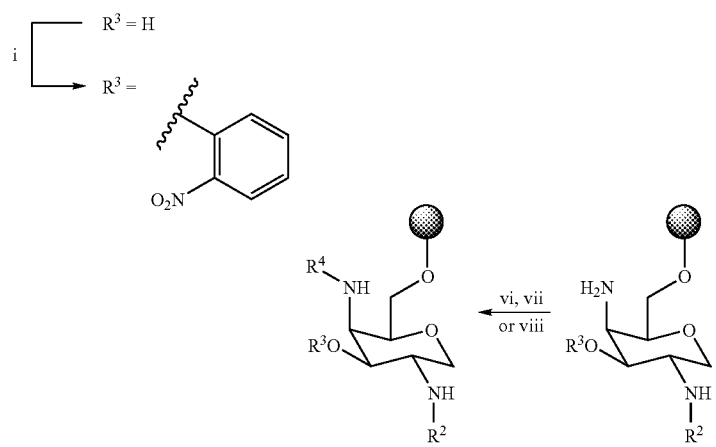

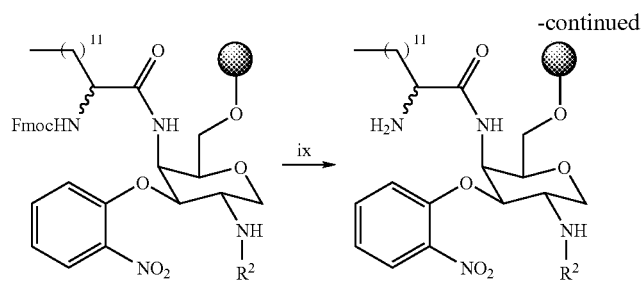

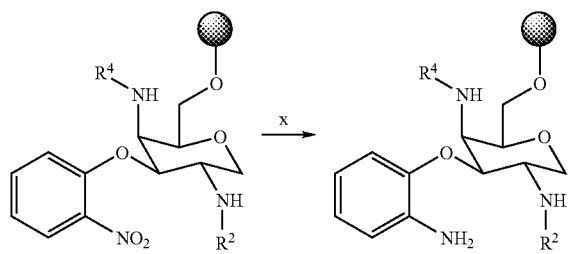

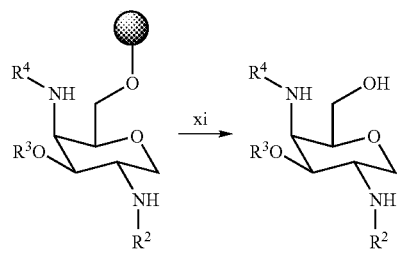

Conditions: i) a) LiO^tBu (0.5 M) in DMF, 10 min. b) 1-Fluoro-2-nitrobenzene (0.5 M) in DMF, 20 min., 3 cycles ii) 5% NH$_2$NH$_2$·H$_2$O in DMF, 1 h iii) 4-Chloro-3-(trifluoromethyl)phenyl isocyanate (0.15 M) in DMF, o/n iv) 4-(Trifluoromethyl)benzenesulfonyl chloride (0.1 M) and DIPEA (0.2 M) in DCM, o/n v) LiO^tBu (0.2 M) and DTT (0.2 M) in DMF, 6 h vi) Aldehyde (0.2 M), NaCNBH$_3$ (0.175 M) in THF/MeOH/AcOH (2:2:1), o/n vii) Biphenyl-4-sulfonyl chloride (67.2 mM) and DIPEA (0.1348 M) in DCM, o/n viii) Acid (0.25 M), HBTU (0.25 M) and DIPEA (0.5 M) in DMF, o/n ix) 20% piperidine in DMF, 1 h, 2 cycles x) SnCl$_2$·2H$_2$O (2.0 M) in DMF, o/n xi) 10% TFA, 20% Et$_3$SiH in DCM.

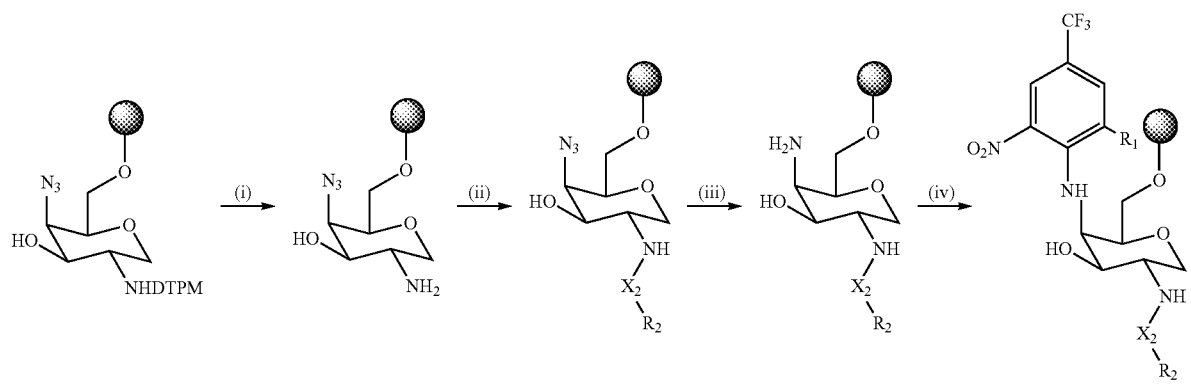

TG26

-continued

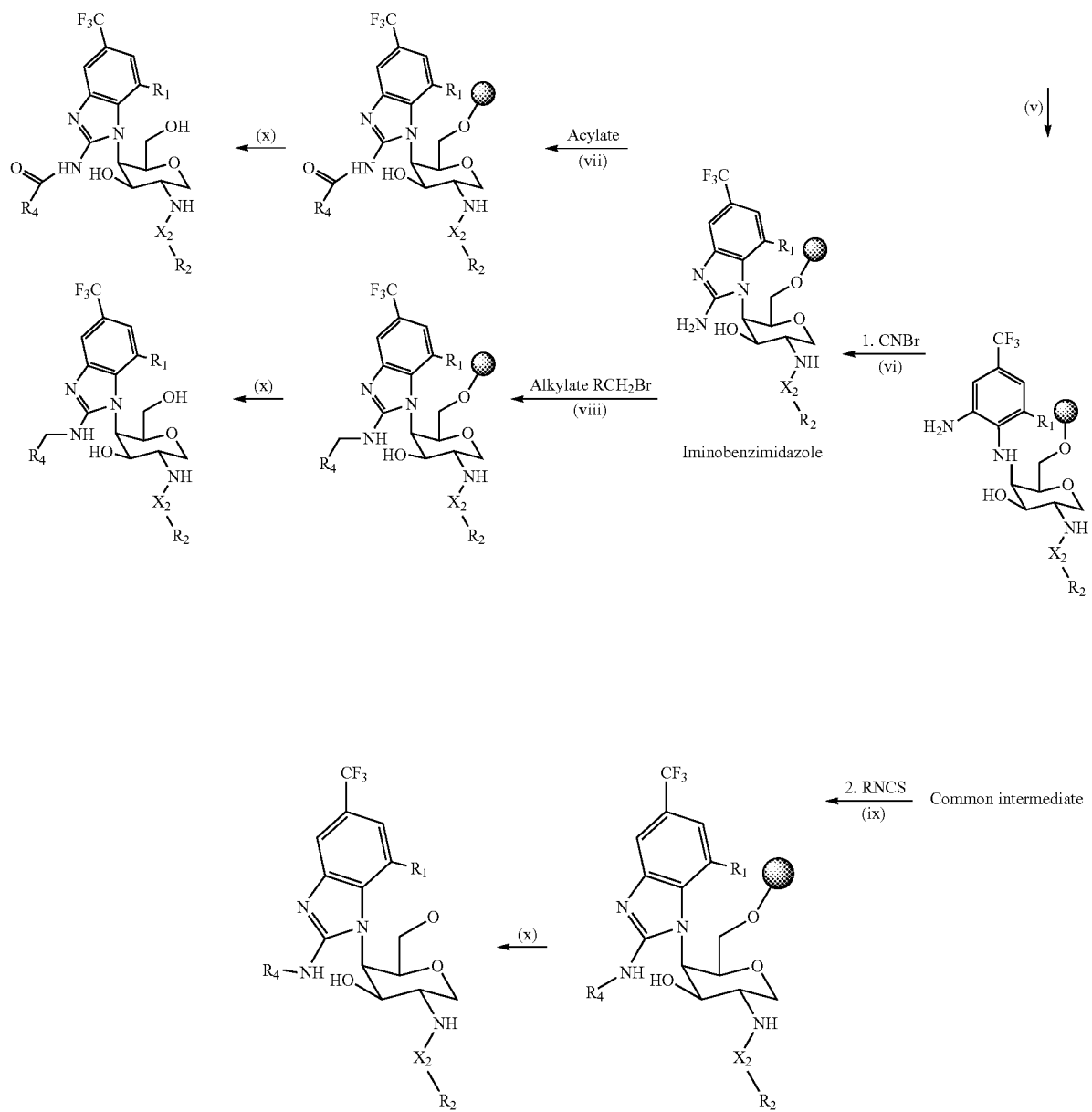

Conditions: (i) 5% NH$_2$NH$_2$·H$_2$O in DMF, 1.5 h (ii) 4-chloro-3-trifluoromethyl isocyanate in DMF at room temperature overnight or 4-trifluoromethyl sulphonyl chloride (2 eq) and DIPEA (4 eq) in DCM overnight (iii) DTT (0.2M) and Li-t-BuO (0.2M) in DMF at room temperature overnight (iv) 4-fluoro-3-nitro-benzotrifluoride (5 eq) or 3-chloro-4-fluoro-5-nitro-benzotrifluoride (3.5 eq) and DIPEA (0.25M) in DMF at 50° C. overnight (v) SnCl$_2$·2H$_2$O (2.0M) in DMF overnight (vi) CNBr (1.0M) in DCM (vii) Amino acid (3 eq) and DIPEA (4 eq) in DMF with HBTU solution (3 eq) and shake overnight (viii) ArCH$_2$Br (5 eq, 0.4M) and DIPEA (10 eq, 0.8M) in DMF at room temperature overnight (ix) Isothiocyanate (10 eq) in DMF for 4 h then drain and add DIC in DMF and shake overnight (x) 10% TFA/20% Et$_3$Si/70% DCM for 3 h and treat dried product with saturated NH$_3$ in methanol solution for 2 h.

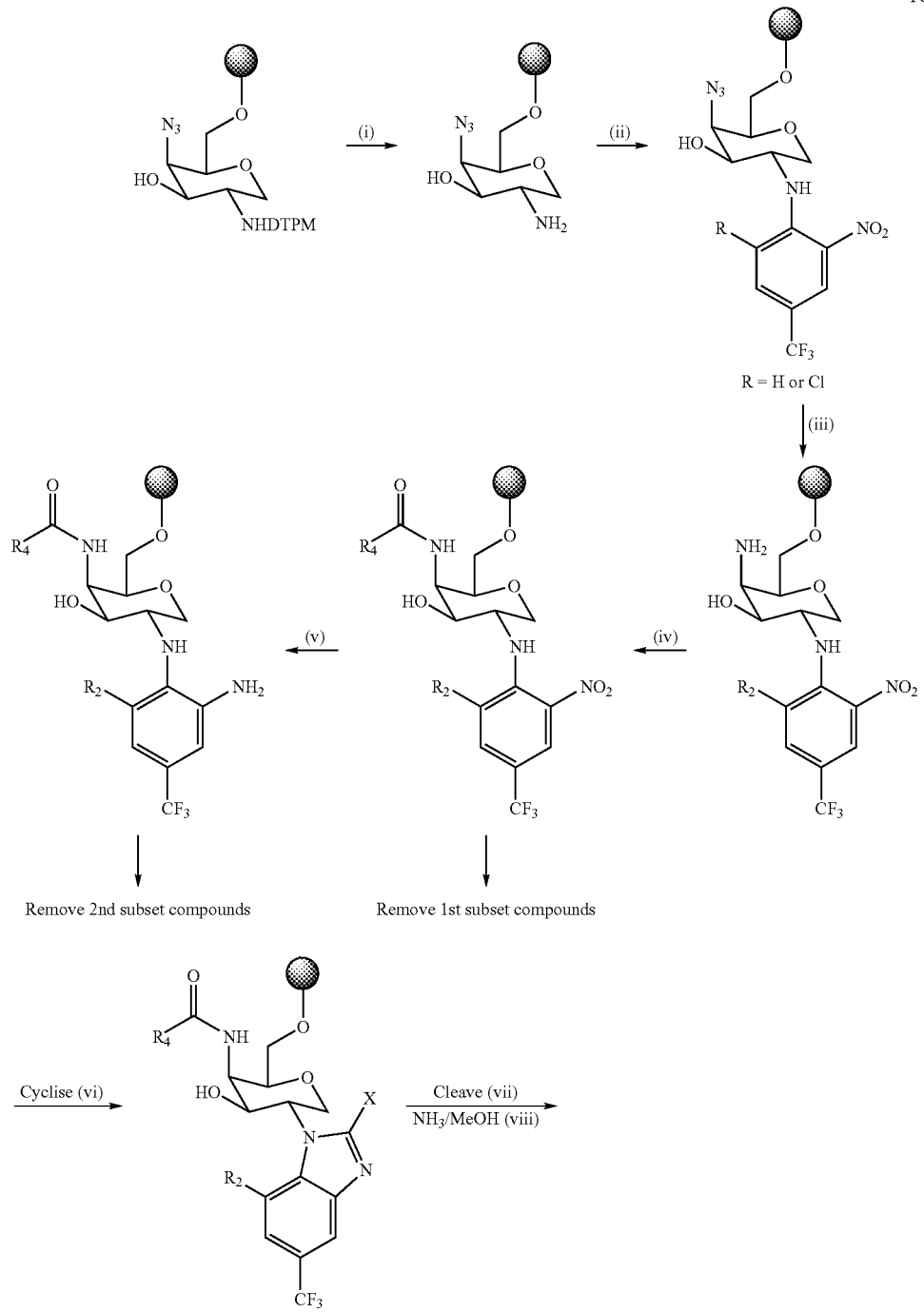

X = H for benzimidazole
OH for benzimidazolone
SH for thiobenzimidazole
NH₂ for iminobenzimidazole Conditions: (i) 5% NH₂NH₂·H₂O in DMF, 1.5 h (ii) 4-fluoro-3-nitro-benzotrifluoride or 3-chloro-4-fluoro-5-nitro-benzotrifluoride (0.25M) and DIPEA (0.25M) in DMF at 50° C. overnight (iii) DTT (1.2M) and triethylamine (2.7M) in DMF at room temperature overnight (iv) Amino acid (3 eq) and DIPEA (4 eq) in DMF with HBTU solution (3 eq) and shake overnight (v) SnCl₂·2H₂O (2.15M) in DMF overnight (vi) p-toluene sulfonic acid monohydrate in trimethylorthoformate (for benzimidazole), 1,1-carbonyldiimidazole (0.5M) in DCM (for benzimidazolone), 1,1-thiocarbonyldiimidazole (0.5M) in THF (for thiobenzimidazole), CNBr (0.5M) in DCM (for iminobenzimidazole) (vii) 10% TFA/20% Et₃Si/70% DCM for 3 h (viii) Saturated NH₃ in methanol solution for 2 h

EXPERIMENTAL

General Resin Preparation Common to Each Library

Preparation of TCA Resin

To Wang resin (20 g, loading: 0.9 mmol/g, 18.0 mmol, dried over $P_2O_5$ overnight) was added dry DCM (200 ml) and dry trichloroacetonitrile (0.32 mol, 17.7 equiv.). The resin suspension was cooled in an ice water bath and gently stirred for 15 min. DBU (13.4 mmol, 0.74 equiv.) was then added dropwise over 15 min. The resulting suspension was then gently stirred at 0° C. with occasional shaking for 1 h to give a dark brown suspension. The resin was then filtered in the glove box and washed with dry DMF (×3), dry THF (×3) and dry DCM (×3). The resin was then dried on the high vac over KOH overnight.

Loading of TG Building Block onto TCA Resin

TCA resin (19.6 g, 15.6 mmol) was washed in the glove box with dry THF (×4). A solution of the appropriate building block (46.9 mmol, 3 equiv.) in dry DCM (75 ml) was added to the resin, which was shaken for 3 min. $BF_3 \cdot OEt_2$ (11.0 mmol, 0.7 equiv.) was then added and the resin was shaken for a further 10 min. The resin was drained and washed with dry DCM (×5). The combined filtrate was washed with sat $NaHCO_3$ (500 ml), dried ($MgSO_4$) and the solvent was removed in vacuo to give the recovered building block.

The resin was washed further with dry THF (×4) and dry DCM (×4) and dried in vacuo overnight.

Removal of Para-Chlorobenzoate Group at 3 Position

The resin bound substrate (22.2 g) was treated with a solution of NaOMe (30 mM) in dry THF (310 ml) and dry MeOH (62 ml). The resin was shaken overnight, filtered in the glove box and washed with dry THF (×3), dry THF/acetic acid/dry MeOH (8:1:1, ×5), dry THF (×3) and dry DCM (×3). The resin was dried in vacuo overnight.

Library Production

TG 23

Note: Resin with an SMe group at the anomeric position, as well as hydrogen, was used for this library.

Alkylation at 3 Position with Methyl Iodide

The resin bound substrate was washed in the glove box with dry DMF (×3). A solution of lithium tert-butoxide in dry DMF (0.25 M) was added and the resin was shaken for 10 min. and drained. A solution of methyl iodide in dry DMF (0.25 M) was added and the resin was shaken for 20 min. The resin was then filtered and washed with dry DMF (×3). This cycle was performed an additional two times. The resin was finally washed in the glove box with dry DMF (×3), dry THF/dry MeOH/acetic acid (8:1:1, ×5), dry THF (×3), dry MeOH (×3) and dry DCM (×3). The resin was then dried on the high vac overnight.

Urea Formation

The resin bound substrate was treated with a solution of DIPEA in dry DMF (0.36 M) and shaken at room temperature for 30 min. The resin was drained, washed with dry DMF (×3) and treated with a solution of the isocyanate in dry DMF (0.15 M). The resin was shaken at room temperature overnight, drained and washed with DMF (×3) and DCM (×3).

Sulfonamide Formation

The resin bound substrate was treated with a solution the sulfonyl chloride (0.1 M) and DIPEA (0.2 M) in dry DCM and shaken at room temperature for 2. The resin was drained, washed with dry DCM (×3), MeOH (×3) and DCM (×3).

TG24

Fluoride Displacement at 3 Position

The resin bound substrate was washed in the glove box with dry DMF (×3). A solution of lithium tert-butoxide in dry DMF (0.5 M) was added and the resin was shaken for 10 min. and drained. A solution of 1-fluoro-2-nitrobenzene in dry DMF (0.5 M) was added and the resin was shaken for 20 min. The resin was then filtered and washed with dry DMF (×3). This cycle was repeated twice. The resin was washed in the glove box with dry DMF (×3), dry THF/dry MeOH/acetic acid (8:1:1, ×3), dry THF (×3), dry MeOH (×3) and dry DCM (×3). The resin was then dried on the high vac overnight.

Removal of DTPM Group at 2 Position

The resin bound substrate was treated with a solution of 5% hydrazine hydrate in DMF and shaken at room temperature for 1 h. The resin was drained, washed with DMF (×5) and DCM (×3) and dried in vacuo.

Urea Formation at 2 Position

The resin bound substrate was washed in the glove box with dry DMF (×3). A solution of 4-chloro-3-(trifluoromethyl)phenyl isocyanate in dry DMF (0.15 M, 1.9 equiv.) was added and the resin was shaken at room temperature overnight. The resin was filtered in the glove box, washed with dry DMF (×3) and dry DCM (×3) and dried in vacuo. Compounds with a free hydroxyl at the 3-position were subsequently treated in the following manner: the resin was then swollen in dry THF and treated with a solution of NaOMe in dry MeOH (0.3 M). The resin was heated at 70° C. and under nitrogen for 4 h, allowed to cool, transferred into a solid phase vessel with dry THF and washed with dry THF (×3), dry MeOH (×3) and dry DCM (×3). The resin was then dried on the high vac overnight.

Sulfonamide Formation at 2 Position

The resin bound substrate was treated in the glove box with a solution of 4-(trifluoromethyl)-benzenesulfonyl chloride (0.11 M, 2 eq) and DIPEA (0.22 M, 4 eq) in dry DCM. The resin was shaken at room temperature overnight, filtered, washed in the glove box with dry DCM (×3), dry MeOH (×3) and dry DCM (×3) and dried in vacuo.

Reductive Amination at 4 Position

A solution of aldehyde (0.2 M) and sodium cyanoborohydride (0.175 M) in dry THF/dry MeOH/acetic acid (2:2:1) was added to each resin bound substrate. The resins were shaken at room temperature overnight, filtered and washed with THF/MeOH (1:3, ×3), DMF/MeOH (1:3, ×3), DCM/MeOH (1:3, ×3) and DCM (×3).

Sulfonamide Formation at 4 Position

To each resin bound substrate was added a solution of biphenyl-4-sulfonyl chloride (76.2 mM) and DIPEA (0.135 M) in dry DCM. The resins were shaken at room temperature overnight, filtered and washed with DCM (×3), MeOH (×3) and DCM (×3).

Reduction of Aromatic Nitro Group with Tin Chloride

Each resin bound substrate was washed with DMF (×2), then treated with a solution of $SnCl_2 \cdot 2H_2O$ in DMF (2.0 M) and shaken at room temperature overnight. The resins were filtered and washed with DMF (×3), DMF/MeOH (1:1, ×3), DMF (×3), DMF/MeOH (1:1, ×3) and DCM (×3).

TG25

Fluoride Displacement at 3 Position

The resin bound substrate was washed in the glove box with dry DMF (×3). A solution of lithium tert-butoxide in dry DMF (0.5 M) was added and the resin was shaken for 10 min. and drained. A solution of 1-fluoro-2-nitrobenzene in dry DMF-(0.5 M) was added and the resin was shaken for 20 min. The resin was then filtered and washed with dry DMF (×3). This cycle was performed an addition two times. The resin was finally washed in the glove box with dry DMF (×3), dry THF/dry MeOH/acetic acid (8:1:1, ×5), dry THF (×3), dry MeOH (×3) and dry DCM (×3). The resin was then dried on the high vac overnight.

Removal of DTPM Group at 2 Position

The resin bound substrate was treated with a solution of 5% hydrazine hydrate in DMT and shaken at room temperature for 1 h. The resin was drained, washed with DMF (×5) and DCM (×3) and dried in vacuo.

Urea Formation at 2 Position

The resin bound substrate was washed in the glove box with dry DMF (×3). A solution of 4-chloro-3-(trifluoromethyl)phenyl isocyanate in dry DMF (0.15 M, 1.9 equiv.) was added and the resin was shaken at room temperature overnight. The resin was filtered in the glove box, washed with dry DMF (×3) and dry DCM (×3) and dried in vacuo. Compounds with a free hydroxyl at the 3-position were subsequently treated in the following manner: the resin was then swollen in dry THF and treated with a solution of NaOMe in dry MeOH (0.3 M). The resin was heated at 70° C. and under nitrogen for 4 h, allowed to cool, transferred into a solid phase vessel with dry THF and washed with dry THF (×3), dry MeOH (×3) and dry DCM (×3). The resin was then dried on the high vac overnight.

Sulfonamide Formation at 2 Position

The resin bound substrate was treated in the glove box with a solution of 4-(trifluoromethyl)-benzenesulfonyl chloride (0.11 M, 2 eq) and DIPEA (0.22 M, 4 eq) in dry DCM. The resin was shaken at room temperature overnight, filtered, washed in the glove box with dry DCM (×3), dry MeOH (×3) and dry DCM (×3) and dried in vacuo.

Triazole Formation from Alkynes at 4 Position

To each resin bound substrate was added a solution of the alkyne in dry toluene (0.44 M). The resins were heated in test tubes in a graphite bath at 100° C. overnight, allowed to cool, transferred into solid phase tubes in the Bohdan Block with toluene and washed with toluene (×3), THF (×3) and DCM (×3). The resins were dried in vacuo for 2 h. The reaction was repeated.

Triazole Formation from β-Ketoesters at 4 Position

To each resin bound substrate was added a solution of the β-ketoester in dry DMF (0.5 M) followed by a solution of NaOEt in EtOH (0.5 M). The resins were heated in test tubes in a graphite bath at 100° C. overnight, allowed to cool, transferred into solid phase tubes in the Bohdan Block with DMF and washed with DMF (×3), DMF/MeOH (1:1, ×3), DMF (×3), DMF/MeOH (1:1, ×3) and DCM (×3). The resins were dried in vacuo for 2 h. The reaction was repeated for the biphenyl derivatives.

Each resin was then swollen in THF and then treated with a solution of lithium hydroxide monohydrate in water (1.5 M). The resins were shaken on a Merrifield shaker (reactions were not successful when performed using the Bohdan block presumable due to insufficient mixing) at room temperature overnight, drained and washed with THF (×3), MeOH (×3), THF (×3), MeOH (×3) and DCM (×3).

Triazole Formation from 4-Biphenylacetonitrile at 4 Position

To the resin bound substrate was added a solution of 4-biphenylacetonitrile in dry DMF (0.5 M) followed by a solution of NaOEt in EtOH (0.5 M). The resin was heated in a test tube in a graphite bath at 100° C. overnight, allowed to cool, transferred into solid phase tubes in the Bohdan Block with DMF and washed with DMF (×3), DMF/MeOH (1:1, ×3), DMF (×3), DMF/MeOH (1:1, ×3) and DCM (×3). The resin was dried in vacuo for 2 h.

TG26

DTPM Removal

The resin bound substrate was treated with a solution of 5% hydrazine hydrate in DMF and shaken at room temperature for 1.5 h. The resin was drained, washed with DMF (×5) and DCM (×3) and dried in vacuo.

Urea Formation

The resin bound substrate was washed with dry DMF and then the 4-chloro-3-trifluoromethyl isocyanate in DMF added and the reaction shaken overnight. The resin was drained and washed with DMF, MeOH and DCM.

Compounds with a free hydroxyl at the 3-position were subsequently treated in the following manner: The resin bound substrate was shaken for 3 h with a NaOMe solution (0.15M) made by dissolving 260 mg of Na metal in MeOH (15 mL) and mixing with THF (65 mL). The resin was washed with THF (×3), MeOH (×3) and DCM (×3) and dried under vacuum.

Sulphonamide Formation

The resin bound substrate was washed with dry DCM (×3) and DIPEA (4 eq, 0.3M) in DCM added. 4-Trifluoromethyl sulfonylchloride (2 eq, 0.15M) was taken up in DCM and also added to the resin and shaken overnight. The resin was drained and washed with DCM (×3), MeOH (×3) and DCM (×3).

Fluoride Displacement at the 4-Position

Resin bound substrates were treated with a solution of either 4-fluoro-3-nitro-benzotrifluoride (5.40 mmol, 5 eq) or 3-chloro-4-fluoro-5-nitro-benzotrifluoride (3.75 mmol, 3.5 eq) and DIPEA (5.4 mmol) in DMF (15 mL) at 50° C. overnight without shaking. The resins were then transferred into fritted vessels and drained and washed with dry DMF (×3), dry MeOH (×3), dry DCM (×3) and dried in vacuo.

Tin (II) Chloride Nitro Reduction

Each resin bound substrate was washed with DMF (×2), then treated with a solution of $SnCl_2 \cdot 2H_2O$ in DMF (2.0 M) and shaken at room temperature overnight. The resins were drained and washed with DMF (×3), DMF/MeOH (1:1, ×3), DMF (×3), DMF/MeOH (1:1, ×3) and DCM (×3).

Cyclisation to the 4-iminobenzimidazole

Resin bound substrated was washed with anhydrous DCM then treated with cyanogen bromide (1M in DCM) overnight. After this time, the resins were then drained and washed with DCM (×3), MeOH (×3) and DCM (×3).

Acylation of the Iminobenzimidazole (Anhydride/DIC Method)

A solution was made up of each amino acid (1.6 mmol) and DIC (0.125 mL) in DMF (3.8 mL). This was stirred for one hour and then one solution was added to each resin bound substrate and the reaction mixture was shaken overnight. The resins were drained and washed with DMF (×3), MeOH (×3) and DCM (×3).

The resin bound substrates were subsequently treated with a solution of sodium methoxide 0.1 M in THF/MeOH (5:1) overnight then drained and washed with THF (×3), MeOH (×3), THF (×3) and DCM (×3).

Alkylation of the Iminobenzimidazole

Each resin bound substrate was treated with a solution containing a substituted aryl bromide (5 eq, 0.4M) and DIPEA (10 eq, 0.8M) in DMF. The solutions were shaken overnight. The resins were drained and washed with DMF (×3), MeOH (×3) and DCM (×3).

Cyclisation with the Aromatic Isothiocyanates

Resin bound substrate was treated with a solution of an aromatic isothiocyanates (3.08 mmol, 10 eq) in DMF for 4 h and then drained. Following this treatment, a solution of DIC (3.08 mmol, 10 eq) in DMF was added and the reaction mixture was shaken overnight. The resins were then drained and washed with DMF (×3), MeOH (×3) and DCM (×3).

Cyclisation with Decyl Isothiocyanate

The decyl isothiocyanate (6.16 mmol, 20 eq) and DIPEA (9.24 mmol, 30 eq) were taken up in DMF and added to each of the resin bound substrates. The resins were shaken overnight and then drained and washed with DMF (×3). A solution of DIC (20 eq, 1.54M) in DMF was added to each resin and the mixture shaken overnight. The resins were then drained and washed with DMF (×3), MeOH (×3) and DCM (×3).

TG27

DTPM Removal

The resin bound substrate was treated with a solution of 5% hydrazine hydrate in DMF and shaken at room temperature for 1.5 h. The resin was drained, washed with DMF (×5) and DCM (×3) and dried in vacuo.

Fluoride Displacement at the 2-Position

Resin bound substrates were treated with a solution of either 4-fluoro-3-nitro-benzotrifluoride (5.40 mmol, 5 eq) or 3-chloro-4-fluoro-5-nitro-benzotrifluoride (3.75 mmol, 3.5 eq) and DIPEA (5.4 mmol) in DMF (15 mL) at 50° C. overnight without shaking. The resins were then transferred into fritted vessels and drained and washed with dry DMF (×3), dry MeOH (×3), dry DCM (×3) and dried in vacuo.

Tin (II) Chloride Reduction

Resin bound substrate was washed with DMF (×2), then treated with a solution of $SnCl_2.2H_2O$ in DMF (2.0 M) and shaken at room temperature overnight. The resins were filtered and washed with DMF (×3), DMF/MeOH (1:1, ×3), DMF (×3), DMF/MeOH (1:1, ×3) and DCM (×3).

Cyclisation to the Benzimidazole

Resin bound substrate was washed with THF (×3). p-toluenesulfonic acid monohydrate (catalytic) in trimethyl orthoformate and added to each of the resins. After shaking overnight the resins were drained and washed with THF (×3), MeOH (×3) and DCM (×3).

Cyclisation to the Benzimidazolone

Resin bound substrate was washed with DCM (×3). 1,1-carbonyldiimidazole (0.1M) in DCM and added to each of the resins. After shaking overnight the resins were drained and washed with DCM (×3), MeOH (×3) and DCM (×3).

Cyclisation to the Thiobenzimidazoleone

Resin bound substrate was washed with THF (×3). 1,1-thiocarbonyldiimidazole (0.5M) in THF and added to each of the resins. After shaking overnight the resins were drained and washed with THF (×3), MeOH (×3) and DCM (×3).

Cyclisation to the Iminobenzimidazoleone

Resin bound substrate was washed with DCM (×3). A 0.5M solution of cyanogen bromide was added to each of the resins. After shaking overnight the resins were drained and washed with DCM (×3), MeOH (×3) and DCM (×3).

At this point the (benzimidazolone and thiobenzimidazole) resins were treated with a sodium methoxide in THF/MeOH solution (0.04M) to remove any 3-position carbamates/thiocarbamates which may have formed. The resins were then drained and washed with THF (×3), MeOH (×3), THF (×3) and DCM (×3).

TG29

Urea Formation

Resin bound substrate was drained, washed with dry DMF (×3) and treated with a solution of an isocyanate in dry DMF (0.15 M). The resin was shaken at room temperature overnight, drained and washed with DMF (×3) and DCM (×3).

Thiourea Formation

Resin bound substrate was drained, washed with dry DMF (×3) and treated with a solution of an isothiocyanate in dry DMF (0.15 M). The resin was shaken at room temperature overnight, drained and washed with DMF (×3) and DCM (×3).

Examples of the kind of molecules synthesised are shown below. ACL00016124 has been shown to have an MIC of 1 µg/mL against *S. Aureus* in the absence of serum. ACL00016116 has shown MIC's of 4 µg/mL and 16 µg/mL against *S. Aureus* in the absence and presence (5% horse serum) of serum, respectively. Finally, ACL00016105 has demonstrated MIC values from 2-4 µg/mL, against *S. Aureus*, *S. Aureus* MRSA, *E. Faecium*, *E. Faecium* VanB and *E. Faecalis* in the absence of serum.

Biological Test Methods

Antibacterial testing was undertaken at a number of contract research organizations, and methods and procedures for the culture and testing of antibacterials are well documented in the scientific and technical literature. The following general procedures are provided as examples of the methods applied.

Testing was conducted to determine the in vitro antimicrobial activity of a series of compounds synthesised by Alchemia Pty Ltd. The antimicrobial activity of each compound was determined at a single concentration (128 µg/mL) in Mueller Hinton (MH) broth against the ATCC type strain of *Staphylococcus aureus*. Compounds that demonstrate activity at this level were then subjected to MIC determination in *S. aureus* in MH broth in the absence of serum and in the presence of 5% heat inactivated horse serum. Compounds showing activity at concentrations up to 32-64 µg/mL in the presence/absence of serum were then tested for MIC activity against a standard set of 5 microorganisms comprising of ATCC type strains of MRSA, *Enterococcus faecalis*, *Enterococcus faecium*, VRE and *Escherichia coli*. CLSI (formerly NCCLS) microbroth dilution technique was used.

Procedures

Test Solution Preparation

Each compound is initially dissolved in 100 µL of DMSO. Each solution is then diluted further in 0.9 mL of sterile MH broth to give a total volume of 1 mL (1000 µg/mL) This stock solution is then further diluted in MH broth to give a test solution with final concentration of 128 µg/mL using the following formula:

0.5 ml stock in 3.4 ml MH broth

The test solutions are prepared on the same day as initial testing is performed. Remaining stock and test solutions are then stored in labelled containers at −20° C.

Test Organisms

The same series of organisms were tested for all compounds. These include ATCC strains:

*Staphylococcus aureus* ATCC 25923 (fully susceptible)
*Staphylococcus aureus* (MRSA) ATCC 33591
*Enterococcus faecalis* ATCC 29212
*Enterococcus faecium* ATCC 35667
*Escherichia coli* ATCC 25922
*Enterococcus faecalis* ATCC 51299 (VRE)

Each test organism was subcultured from the −70° C. deep freezer onto horse blood agar. The plates were streaked to obtain isolated colonies and incubated at 35° C. in non-$CO_2$ incubator for 24 hours. A second subculture was carried out onto horse blood agar. For each test organism, 1-2 colonies were selected from an 18-24 hour culture and inoculated into 2 ml sterile MH broth. The turbidity was adjusted to 0.5 McFarland standard.

A 1:10 dilution in MH broth (200 µL in 2 ml MH) of the 0.5 McFarland control was prepared. 5 µL of this diluted solution was used to inoculate the trays.

MICs to vancomycin for each test organism were determined in a single series of testing as a means of confirming the test organisms were reacting within defined. MIC parameters.

Activity Against *S. Aureus*

100 μL of test solution was added to each well. The final row on each tray had sterile MH broth only added (positive control). 5 μL of test organism solution was added to each well including the final row. The final well on each row had no organism solution added (negative control). The plate was then sealed and incubated at 35° C. in a non-$CO_2$ incubator for 18-24 hours. The plates were examined for growth after the incubation time.

MIC Against *S. aureus*

Each compound that showed activity against *S. aureus* (inhibition of growth in the well) was tested further to determine the actual MIC. 100 μL of sterile MH broth was added in columns 2-12. 200 μL of test solution was added in column 1. 100 μL was transferred in column 2 giving a ½ dilution. 100 μL from column 2 was then transferred to column 3 (¼ dilution). This dilution was carried on until column 12. A second tray containing the same test solution was inoculated in a similar manner using sterile MH broth with 5% heat inactivated horse serum. 5 μL of organism solution was then added to each well. The plates were then sealed and incubated at 35° C. in a non-$CO_2$ incubator for 18-24 hours. The plates were examined for growth after the incubation time.

MIC Levels Against 5 Organisms

Each compound that showed activity at MIC level at 32 or less in sterile MH broth and at MIC level of 64 or less in the presence of serum was tested to determine full MIC against 5 microorganisms. The trays were prepared in a similar way as mentioned above and incubated at 35° C. in a non-$CO_2$ incubator for 18-24 hours. The plates were examined for growth after the incubation time.

After 18-24 hour incubation 5 μL from each well was then inoculated onto horse blood agar and incubated for 18-24 hours at 35° C. in a non-$CO_2$ incubator.

Plate Examination

If the test organism is sensitive to the compound in the broth the growth will be inhibited. Similarly, if the organism grows on the antibiotic containing medium then it is resistant to this particular antibiotic.

The organisms were scored as follows:

"No Growth"=Sensitive (S)

"Growth"=Resistant (R)

"Scant growth"=SG

All the results were recorded electronically on spreadsheets.

HPLC Separation

All compounds were separated on a Zorbax C18(4.6×50 mm) column.

The liquid phase used was $H_2O$— Acetonitrile in the gradients described below.

5% acetonitrile from 0-1 min then gradient to 100% acetonitrile at 7 min and hold until 12 min for TG 23, 24, 27 and 29.

5% acetonitrile from 0-1 min then gradient to 30% acetonitrile at 3 min, gradient to 60% acetonitrile at 11 min and gradient to 100% acetonitrile at 12 min and hold until 15 min for TG 25

5% acetonitrile from 0-1 min then gradient to 100% $H_2O$ at 7 min and hold until 12 min for TG 26 compounds apart from AL00016098 and AL00016114 which used 5% acetonitrile from 0-1 min then gradient to 40% acetonitrile at 3 min, gradient to 70% acetonitrile at 11 min and gradient to 100% acetonitrile at 12 min and hold until 15 min.

Key to Building Blocks for Tables 1 and 2

TABLE 1

Compounds of formula (1)

RT: retention time/minutes
M + H: mass ion + 1

TABLE 2

Biological activity of compounds of formula (1)

"++": MIC (μg/mL): MIC ≦ 16
"+": MIC (μg/mL): 64 ≧ MIC > 16
"−": MIC (μg/mL): MIC > 64
Blank: not determined

TABLE 1

Compounds of formula (1)

| Compound Number | R1 | R2 | R3 | R4 | RT | M + H |
|---|---|---|---|---|---|---|
| 1 | X1 | X3 | X9 | X10 | 5.27 | 564 |
| 2 | X1 | X8 | X9 | X10 | 5.23 | 552 |
| 3 | X1 | X3 | X9 | X22 | 4.78 | 550 |
| 4 | X1 | X7 | X9 | X12 | 4.18 | 595 |
| 5 | X1 | X8 | X9 | X16 | 6.04 | 540 |
| 6 | X1 | X7 | X9 | X16 | 5.93 | 540 |
| 7 | X2 | X7 | X9 | X16 | 6.29 | 586 |
| 8 | X1 | X7 | X81 | X16 | 6.23 | 554 |
| 9 | X1 | X6 | X9 | X10 | 5.26 | 586 |
| 10 | X2 | X7 | X9 | X10 | 5.22 | 598 |
| 11 | X1 | X7 | X81 | X10 | 5.43 | 566 |
| 12 | X1 | X6 | X9 | X11 | 5.7 | 620 |
| 13 | X1 | X8 | X9 | X11 | 5.32 | 586 |
| 14 | X1 | X7 | X9 | X11 | 5.38 | 586 |
| 15 | X2 | X7 | X9 | X11 | 5.58 | 632 |
| 16 | X1 | X7 | X81 | X11 | 5.63 | 600 |
| 17 | X1 | X6 | X9 | X12 | 4.27 | 629 |
| 18 | X1 | X8 | X9 | X12 | 4.12 | 595 |
| 19 | X2 | X7 | X9 | X12 | 4.37 | 641 |
| 20 | X1 | X7 | X81 | X12 | 4.33 | 609 |
| 21 | X1 | X6 | X9 | X13 | 4.38 | 629 |
| 22 | X1 | X8 | X9 | X13 | 4.18 | 595 |
| 23 | X1 | X7 | X9 | X13 | 4.27 | 595 |
| 24 | X2 | X7 | X9 | X13 | 4.28 | 641 |
| 25 | X1 | X7 | X81 | X13 | 4.32 | 609 |
| 26 | X1 | X6 | X9 | X17 | 4.78 | 631 |
| 27 | X1 | X8 | X9 | X17 | 4.72 | 597 |
| 28 | X1 | X7 | X9 | X17 | 4.68 | 597 |
| 29 | X2 | X7 | X9 | X17 | 5.12 | 643 |
| 30 | X1 | X7 | X81 | X17 | 4.93 | 611 |
| 31 | X1 | X6 | X9 | X14 | 5.77 | 560 |
| 32 | X1 | X8 | X9 | X14 | 5.53 | 526 |
| 33 | X1 | X7 | X9 | X14 | 5.58 | 526 |
| 34 | X2 | X7 | X9 | X14 | 5.79 | 572 |
| 35 | X1 | X7 | X81 | X14 | 5.84 | 540 |
| 36 | X1 | X8 | X9 | X15 | 5.18 + 4.68 | 526 |
| 37 | X1 | X7 | X9 | X15 | 4.71 + 5.23 | 526 |
| 38 | X1 | X7 | X81 | X15 | 5.27 | 540 |
| 39 | X1 | X6 | X9 | X19 | 5.18 | 570 |
| 40 | X1 | X8 | X9 | X19 | 5.02 | 536 |
| 41 | X1 | X7 | X9 | X19 | 4.98 | 536 |
| 42 | X2 | X7 | X9 | X19 | 5.17 | 582 |
| 43 | X1 | X7 | X81 | X19 | 5.23 | 550 |
| 44 | X1 | X6 | X9 | X18 | 5.32 | 602 |
| 45 | X1 | X8 | X9 | X18 | 5.13 | 568 |
| 46 | X1 | X7 | X9 | X18 | 5.12 | 568 |
| 47 | X2 | X7 | X9 | X18 | 5.33 | 614 |
| 48 | X1 | X7 | X81 | X18 | 5.37 | 582 |
| 49 | X1 | X3 | X9 | X21 | 4.82 | 584 |
| 50 | X1 | X3 | X9 | X23 | 5.27 | 524 |

TABLE 1-continued

Compounds of formula (1)

| Compound Number | R1 | R2 | R3 | R4 | RT | M + H |
|---|---|---|---|---|---|---|
| 51 | X1 | X3 | X9 | X24 | 4.63 | 567 |
| 52 | X1 | X3 | X9 | X25 | 5.22 | 600 |
| 53 | X1 | X7 | X9 | X21 | 4.68 | 571 |
| 54 | X1 | X7 | X9 | X22 | 4.42 | 537 |
| 55 | X1 | X7 | X9 | X23 | 4.93 | 511 |
| 56 | X1 | X7 | X9 | X24 | 4.67 | 554 |
| 57 | X1 | X7 | X9 | X25 | 5.28 | 587 |
| 58 | X1 | X3 | X20 | X21 | 5.27 | 675 |
| 59 | X1 | X3 | X20 | X22 | 5.08 | 641 |
| 60 | X1 | X3 | X20 | X23 | 5.72 | 615 |
| 61 | X1 | X3 | X20 | X24 | 5.64 | 658 |
| 62 | X1 | X3 | X20 | X25 | 5.42 | 691 |
| 63 | X1 | X7 | X20 | X21 | 5.14 | 662 |
| 64 | X1 | X7 | X20 | X22 | 4.87 | 628 |
| 65 | X1 | X7 | X20 | X23 | 5.43 | 602 |
| 66 | X1 | X7 | X20 | X24 | 5.37 | 645 |
| 67 | X1 | X7 | X20 | X25 | 5.38 | 678 |
| 68 | X1 | X3 | X20 | X16 | 6.18 | 643 |
| 69 | X1 | X3 | X20 | X10 | 5.43 | 655 |
| 70 | X1 | X3 | X20 | X12 | 4.67 | 698 |
| 71 | X1 | X3 | X20 | X12 | 4.88 | 698 |
| 72 | X1 | X3 | X20 | X13 | 4.52 | 698 |
| 73 | X1 | X3 | X20 | X17 | 5.6 | 700 |
| 74 | X1 | X3 | X20 | X17 | 6.18 | 700 |
| 75 | X1 | X3 | X20 | X17 | 5.58 | 700 |
| 76 | X1 | X7 | X20 | X16 | 5.33 | 630 |
| 77 | X1 | X7 | X20 | X10 | 4.47 | 642 |
| 78 | X1 | X7 | X20 | X12 | 4.68 | 685 |
| 79 | X1 | X7 | X20 | X12 | 4.47 | 685 |
| 80 | X1 | X7 | X20 | X13 | 5.53 | 685 |
| 81 | X1 | X7 | X20 | X17 | 1 | 687 |
| 82 | X1 | X3 | X9 | X16 | 6.04 | 552 |
| 83 | X1 | X4 | X9 | X16 | 5.72 | 518 |
| 84 | X1 | X5 | X9 | X16 | 5.78 | 518 |
| 85 | X1 | X77 | X9 | X16 | 5.78 | 534 |
| 86 | X1 | X74 | X9 | X16 | 5.88 | 518 |
| 87 | X1 | X75 | X9 | X16 | 5.99 | 534 |
| 88 | X1 | X76 | X9 | X16 | 5.97 | 534 |
| 89 | X1 | X78 | X9 | X16 | 4.47 | 373 |
| 90 | X1 | X5 | X9 | X10 | 4.97 | 530 |
| 91 | X1 | X77 | X9 | X10 | 5.13 | 546 |
| 92 | X1 | X74 | X9 | X10 | 5.08 | 530 |
| 93 | X1 | X75 | X9 | X10 | 5.18 | 546 |
| 94 | X1 | X78 | X9 | X10 | 3.82 | 385 |
| 95 | X1 | X5 | X9 | X12 | 4.42 | 573 |
| 96 | X1 | X74 | X9 | X12 | 4.47 | 573 |
| 97 | X1 | X75 | X9 | X12 | 4.53 | 589 |
| 98 | X1 | X76 | X9 | X12 | 4.47 | 589 |
| 99 | X1 | X78 | X9 | X12 | 3.47 | 428 |
| 100 | X1 | X3 | X9 | X13 | 4.38 | 607 |
| 101 | X1 | X4 | X9 | X13 | 4.22 | 573 |
| 102 | X1 | X5 | X9 | X13 | 4.28 | 573 |
| 103 | X1 | X77 | X9 | X13 | 4.27 | 589 |
| 104 | X1 | X74 | X9 | X13 | 4.33 | 573 |
| 105 | X1 | X76 | X9 | X13 | 4.43 | 589 |
| 106 | X1 | X78 | X9 | X13 | 3.22 | 428 |
| 107 | X1 | X3 | X9 | X17 | 5.33 | 609 |
| 108 | X1 | X4 | X9 | X17 | 5.07 | 575 |
| 109 | X1 | X5 | X9 | X17 | 4.97 | 575 |
| 110 | X1 | X77 | X9 | X17 | 5.12 | 591 |
| 111 | X1 | X74 | X9 | X17 | 5.07 | 575 |
| 112 | X1 | X4 | X9 | X15 | 5.37 | 504 |
| 113 | X1 | X5 | X9 | X15 | 5.43 | 504 |
| 114 | X1 | X77 | X9 | X15 | 5.48 | 520 |
| 115 | X1 | X74 | X9 | X15 | 5.54 | 504 |
| 116 | X1 | X75 | X9 | X15 | 5.57 | 520 |
| 117 | X1 | X76 | X9 | X15 | 5.69 | 520 |
| 118 | X1 | X78 | X9 | X15 | 4.18 | 359 |
| 119 | X1 | X3 | X9 | X19 | 5.07 | 548 |
| 120 | X1 | X5 | X9 | X19 | 4.88 | 514 |
| 121 | X1 | X77 | X9 | X19 | 4.87 | 530 |
| 122 | X1 | X74 | X9 | X19 | 4.92 | 514 |
| 123 | X1 | X75 | X9 | X19 | 5.03 | 530 |
| 124 | X1 | X76 | X9 | X19 | 5.13 | 530 |
| 125 | X1 | X78 | X9 | X19 | 3.68 | 369 |
| 126 | X1 | X3 | X9 | X18 | 5.23 | 580 |
| 127 | X1 | X4 | X9 | X18 | 5.08 | 546 |
| 128 | X1 | X5 | X9 | X18 | 5.02 | 546 |
| 129 | X1 | X77 | X9 | X18 | 5.13 | 562 |
| 130 | X1 | X74 | X9 | X18 | 5.17 | 546 |
| 131 | X1 | X75 | X9 | X18 | 5.13 | 562 |
| 132 | X1 | X78 | X9 | X18 | 3.87 | 401 |
| 133 | X1 | X3 | X9 | X80 | 5.54 | 629 |
| 134 | X1 | X4 | X9 | X80 | 5.23 | 595 |
| 135 | X1 | X5 | X9 | X80 | 5.33 | 595 |
| 136 | X1 | X77 | X9 | X80 | 5.27 | 611 |
| 137 | X1 | X74 | X9 | X80 | 5.33 | 595 |
| 138 | X1 | X75 | X9 | X80 | 5.37 | 611 |
| 139 | X1 | X76 | X9 | X80 | 5.48 | 611 |
| 140 | X1 | X78 | X9 | X80 | 4.22 | 450 |
| 141 | X1 | X3 | X9 | X79 | 5.33 | 544 |
| 142 | X1 | X4 | X9 | X79 | 5.02 | 510 |
| 143 | X1 | X5 | X9 | X79 | 5.13 | 510 |
| 144 | X1 | X77 | X9 | X79 | 5.07 | 526 |
| 145 | X1 | X74 | X9 | X79 | 5.1 | 510 |
| 146 | X1 | X75 | X9 | X79 | 5.17 | 526 |
| 147 | X1 | X76 | X9 | X79 | 5.33 | 526 |
| 148 | X1 | X78 | X9 | X79 | 3.82 | 365 |
| 149 | X1 | X65 | X9 | X10 | 5.01 | 528 |
| 150 | X1 | X67 | X9 | X10 | 5 | 544 |
| 151 | X1 | X63 | X9 | X10 | 4.17 | 527 |
| 152 | X1 | X61 | X9 | X10 | 4.87 | 512 |
| 153 | X1 | X66 | X9 | X10 | 5.21 | 562 |
| 154 | X1 | X68 | X9 | X10 | 5.39 | 578 |
| 155 | X1 | X64 | X9 | X10 | 4.67 | 561 |
| 156 | X1 | X62 | X9 | X10 | 5.28 | 546 |
| 157 | X1 | X65 | X9 | X12 | 4.18 | 571 |
| 158 | X1 | X67 | X9 | X12 | 4.17 | 587 |
| 159 | X1 | X63 | X9 | X12 | 3.53 | 570 |
| 160 | X1 | X61 | X9 | X12 | 4.12 | 555 |
| 161 | X1 | X66 | X9 | X12 | 4.34 | 605 |
| 162 | X1 | X68 | X9 | X12 | 4.43 | 621 |
| 163 | X1 | X64 | X9 | X12 | 4.07 | 604 |
| 164 | X1 | X62 | X9 | X12 | 4.33 | 589 |
| 165 | X1 | X65 | X9 | X16 | 5.63 | 516 |
| 166 | X1 | X67 | X9 | X16 | 5.84 | 532 |
| 167 | X1 | X63 | X9 | X16 | 4.63 | 515 |
| 168 | X1 | X61 | X9 | X16 | 5.68 | 500 |
| 169 | X1 | X66 | X9 | X16 | 6.14 | 550 |
| 170 | X1 | X68 | X9 | X16 | 6.34 | 566 |
| 171 | X1 | X64 | X9 | X16 | 5.38 | 549 |
| 172 | X1 | X62 | X9 | X16 | 6.13 | 534 |
| 173 | X1 | X65 | X9 | X15 | 5.27 | 502 |
| 174 | X1 | X67 | X9 | X15 | 5.32 | 518 |
| 175 | X1 | X63 | X9 | X15 | 4.33 | 501 |
| 176 | X1 | X61 | X9 | X15 | 5.32 | 486 |
| 177 | X1 | X66 | X9 | X15 | 5.72 | 536 |
| 178 | X1 | X68 | X9 | X15 | 5.88 | 552 |
| 179 | X1 | X64 | X9 | X15 | 5.13 | 535 |
| 180 | X1 | X62 | X9 | X15 | 5.78 | 520 |
| 181 | X1 | X65 | X9 | X17 | 4.83 | 573 |
| 182 | X1 | X67 | X9 | X17 | 4.77 | 589 |
| 183 | X1 | X63 | X9 | X17 | 4.18 | 572 |
| 184 | X1 | X61 | X9 | X17 | 4.77 | 557 |
| 185 | X1 | X66 | X9 | X17 | 5.03 | 607 |
| 186 | X1 | X68 | X9 | X17 | 4.97 | 623 |
| 187 | X1 | X64 | X9 | X17 | 4.83 | 606 |
| 188 | X1 | X62 | X9 | X17 | 4.77 | 591 |
| 189 | X1 | X69 | X9 | X10 | 5.77 | 532 |
| 190 | X1 | X70 | X9 | X10 | 6.77 | 566 |
| 191 | X1 | X69 | X9 | X12 | 7.77 | 575 |
| 192 | X1 | X70 | X9 | X12 | 8.77 | 609 |
| 193 | X1 | X69 | X9 | X16 | 9.77 | 520 |
| 194 | X1 | X70 | X9 | X16 | 10.77 | 554 |
| 195 | X1 | X69 | X9 | X15 | 11.77 | 506 |
| 196 | X1 | X70 | X9 | X15 | 12.77 | 540 |
| 197 | X1 | X69 | X9 | X17 | 13.77 | 577 |
| 198 | X1 | X70 | X9 | X17 | 14.77 | 611 |
| 199 | X1 | X71 | X9 | X10 | 15.77 | 502 |
| 200 | X1 | X72 | X9 | X10 | 16.77 | 536 |
| 201 | X1 | X71 | X9 | X12 | 17.77 | 545 |
| 202 | X1 | X72 | X9 | X12 | 18.77 | 579 |

TABLE 1-continued

Compounds of formula (1)

| Compound Number | R1 | R2 | R3 | R4 | RT | M + H |
|---|---|---|---|---|---|---|
| 203 | X1 | X71 | X9 | X16 | 19.77 | 490 |
| 204 | X1 | X72 | X9 | X16 | 20.77 | 524 |
| 205 | X1 | X71 | X9 | X15 | 21.77 | 476 |
| 206 | X1 | X72 | X9 | X15 | 22.77 | 510 |
| 207 | X1 | X71 | X9 | X17 | 23.77 | 547 |
| 208 | X1 | X3 | X9 | X27 | 5.33 + 5.48 | 588 |
| 209 | X1 | X3 | X9 | X27 | 5.42 | 588 |
| 210 | X1 | X7 | X9 | X27 | 7.98 + 8.63 | 575 |
| 211 | X1 | X7 | X9 | X27 | 8.09 + 8.84 | 575 |
| 212 | X1 | X3 | X20 | X27 | 9.68 | 679 |
| 213 | X1 | X3 | X20 | X27 | 10.57 | 679 |
| 214 | X1 | X7 | X20 | X27 | 9.52 + 10.06 | 666 |
| 215 | X1 | X3 | X9 | X26 | 8.02 + 8.76 | 580 |
| 216 | X1 | X3 | X9 | X26 | 8.72 | 580 |
| 217 | X1 | X7 | X9 | X26 | 7.27 + 8.09 | 567 |
| 218 | X1 | X7 | X9 | X26 | 7.98 | 567 |
| 219 | X1 | X3 | X20 | X26 | 9.2 | 671 |
| 220 | X1 | X3 | X20 | X26 | 9.91 | 671 |
| 221 | X1 | X7 | X20 | X26 | 9.01 + 9.63 | 658 |
| 222 | X1 | X7 | X20 | X26 | 9.54 | 658 |
| 223 | X1 | X3 | X9 | X31 | 7.45 | 632 |
| 224 | X1 | X7 | X9 | X31 | 6.15 + 6.57 | 619 |
| 225 | X1 | X3 | X9 | X29 | 6.32 + 6.67 | 590 |
| 226 | X1 | X7 | X9 | X29 | 5.26 | 577 |
| 227 | X1 | X7 | X9 | X28 | 7.8 | 590 |
| 235 | X1 | X3 | X9 | X53 | 6.68 | 793 |
| 236 | X1 | X3 | X9 | X55 | 5.23 | 777 |
| 237 | X1 | X3 | X9 | X57 | 5.63 | 791 |
| 238 | X1 | X3 | X9 | X59 | 5.54 | 791 |
| 239 | X1 | X7 | X9 | X53 | 6.68 | 780 |
| 240 | X1 | X7 | X9 | X55 | 5.32 | 764 |
| 241 | X1 | X7 | X9 | X57 | 5.67 | 778 |
| 242 | X1 | X7 | X9 | X59 | 5.78 | 778 |
| 243 | X1 | X3 | X9 | X33 | 6.23 | 678 |
| 244 | X1 | X3 | X9 | X35 | 6.23 | 712 |
| 245 | X1 | X3 | X9 | X37 | 5.03 | 720 |
| 246 | X1 | X3 | X9 | X41 | 5.57 | 658 |
| 247 | X1 | X3 | X9 | X43 | 5.39 | 692 |
| 248 | X1 | X3 | X9 | X45 | 5.52 | 714 |
| 249 | X1 | X3 | X9 | X51 | 5.53 | 750 |
| 250 | X1 | X3 | X9 | X47 | 5.27 | 734 |
| 251 | X1 | X3 | X9 | X49 | 6.29 | 708 |
| 252 | X1 | X3 | X9 | X34 | 6.53 | 712 |
| 253 | X1 | X3 | X9 | X36 | 6.49 | 746 |
| 254 | X1 | X3 | X9 | X38 | 5.28 | 754 |
| 255 | X1 | X3 | X9 | X42 | 5.82 | 692 |
| 256 | X1 | X3 | X9 | X44 | 5.83 | 726 |
| 257 | X1 | X3 | X9 | X46 | 8.04 | 748 |
| 258 | X1 | X3 | X9 | X52 | 5.74 | 784 |
| 259 | X1 | X3 | X9 | X48 | 5.74 | 768 |
| 260 | X1 | X3 | X9 | X50 | 5.67 | 742 |
| 261 | X1 | X3 | X9 | X50 | 5.78 | 742 |
| 262 | X1 | X7 | X9 | X33 | 5.93 | 665 |
| 263 | X1 | X7 | X9 | X35 | 5.88 | 699 |
| 264 | X1 | X7 | X9 | X37 | 4.77 | 707 |
| 265 | X1 | X7 | X9 | X41 | 4.83 | 645 |
| 266 | X1 | X7 | X9 | X43 | 5.37 | 679 |
| 267 | X1 | X7 | X9 | X45 | 5.23 | 701 |
| 268 | X1 | X7 | X9 | X51 | 5.27 | 737 |
| 269 | X1 | X7 | X9 | X47 | 4.93 | 721 |
| 270 | X1 | X7 | X9 | X49 | 6.28 | 695 |
| 271 | X1 | X7 | X9 | X34 | 6.24 | 699 |
| 272 | X1 | X7 | X9 | X36 | 6.48 | 733 |
| 273 | X1 | X7 | X9 | X38 | 4.98 | 741 |
| 274 | X1 | X7 | X9 | X42 | 5.32 | 679 |
| 275 | X1 | X7 | X9 | X44 | 5.53 | 713 |
| 276 | X1 | X7 | X9 | X46 | 5.72 | 735 |
| 277 | X1 | X7 | X9 | X52 | 5.43 | 771 |
| 278 | X1 | X7 | X9 | X48 | 5.47 | 755 |
| 279 | X1 | X7 | X9 | X50 | 1 | 729 |

TABLE 2

Biological activity of compounds of formula (1)

| Compound number | S. Aureus 25923 activity | S. Aureus 33591 MRSA activity | E. Faecium 35667 activity | E. Faecium 51299 VanB activity | E. Fecalis 29212 activity |
|---|---|---|---|---|---|
| 7 | + | + | − | − | − |
| 8 | + | − | − | − | − |
| 12 | + | | | | |
| 26 | + | | | | |
| 27 | + | | | | |
| 29 | ++ | | | | |
| 30 | + | | | | |
| 50 | + | + | + | − | + |
| 62 | + | ++ | − | − | − |
| 69 | + | − | − | − | − |
| 70 | + | ++ | + | − | + |
| 71 | ++ | ++ | ++ | + | + |
| 72 | ++ | | | | |
| 73 | ++ | ++ | ++ | + | ++ |
| 74 | + | + | + | + | − |
| 75 | ++ | | | | |
| 79 | + | + | − | − | − |
| 88 | + | + | + | + | + |
| 107 | ++ | ++ | + | + | + |
| 108 | + | + | − | − | − |
| 109 | ++ | + | − | − | − |
| 153 | + | + | − | − | + |
| 155 | + | + | − | − | − |
| 156 | + | − | + | − | − |
| 161 | + | + | − | − | + |
| 163 | + | + | − | − | + |
| 169 | + | + | + | + | + |
| 170 | − | ++ | + | ++ | − |
| 171 | + | + | − | − | − |
| 172 | + | + | − | − | − |
| 177 | + | + | + | − | − |
| 178 | + | − | − | − | − |
| 179 | + | − | − | − | − |
| 181 | + | ++ | + | + | + |
| 182 | ++ | ++ | ++ | ++ | ++ |
| 183 | + | − | ++ | − | − |
| 185 | + | ++ | ++ | + | ++ |
| 186 | ++ | + | − | − | + |
| 187 | ++ | ++ | + | ++ | ++ |
| 188 | + | + | − | + | + |
| 197 | ++ | + | + | + | + |
| 198 | + | + | + | + | + |
| 200 | − | + | − | − | − |
| 202 | + | + | + | − | − |
| 207 | + | + | + | + | + |
| 236 | − | ++ | ++ | + | ++ |
| 237 | − | ++ | − | − | ++ |
| 238 | − | ++ | − | − | ++ |
| 240 | ++ | ++ | − | − | ++ |
| 241 | ++ | ++ | ++ | + | ++ |
| 242 | ++ | ++ | ++ | − | ++ |
| 246 | ++ | ++ | + | + | ++ |
| 247 | ++ | ++ | − | ++ | ++ |
| 248 | ++ | ++ | ++ | ++ | ++ |
| 249 | ++ | ++ | ++ | ++ | ++ |
| 251 | ++ | ++ | ++ | ++ | ++ |
| 252 | + | − | − | − | + |
| 253 | − | − | − | − | + |
| 254 | ++ | ++ | − | − | − |
| 255 | ++ | ++ | − | + | ++ |
| 256 | − | − | − | ++ | ++ |
| 258 | ++ | | | | |
| 259 | ++ | | | | |
| 261 | ++ | | | | |
| 262 | + | | | | |
| 263 | ++ | | | | |
| 264 | ++ | | | | |
| 265 | + | | | | |
| 266 | ++ | | | | |
| 267 | ++ | | | | |
| 268 | ++ | | | | |
| 269 | ++ | | | | |
| 270 | ++ | | | | |

TABLE 2-continued
Biological activity of compounds of formula (1)
| Compound number | S. Aureus 25923 activity | S. Aureus 33591 MRSA activity | E. Faecium 35667 activity | E. Faecium 51299 VanB activity | E. Fecalis 29212 activity |
|---|---|---|---|---|---|
| 271 | ++ | | | | |
| 272 | ++ | | | | |
| 273 | ++ | | | | |
| 274 | ++ | | | | |
| 275 | ++ | | | | |
| 276 | + | | | | |
| 277 | + | | | | |
| 278 | ++ | | | | |
| 279 | ++ | | | | |
FIG. 1: Sidearms for Table 1.
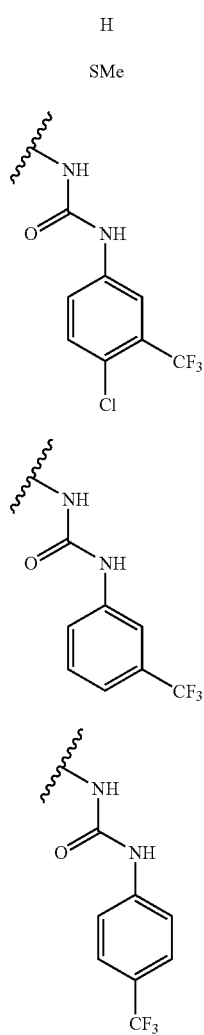
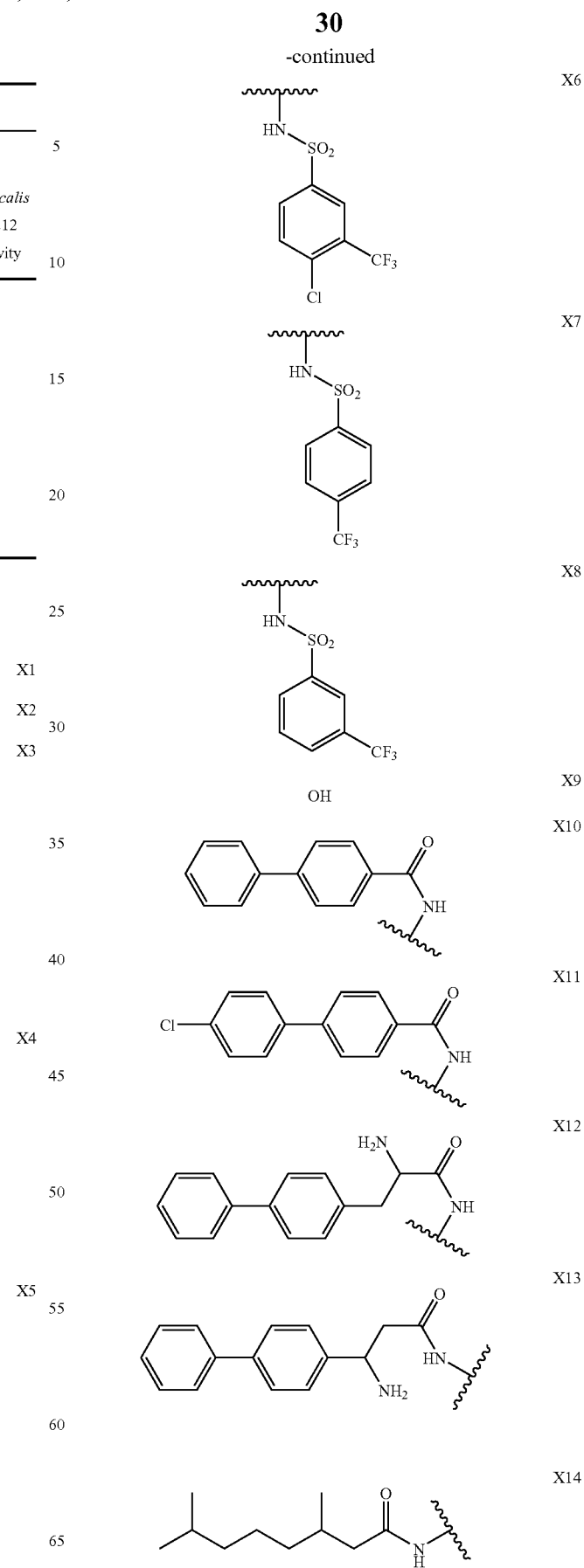

-continued
X15 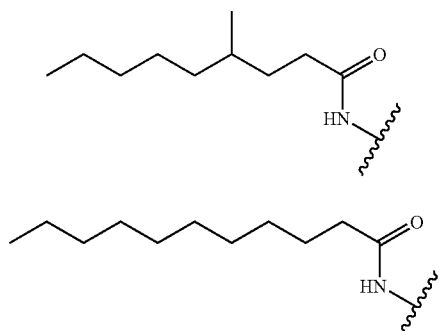
X16 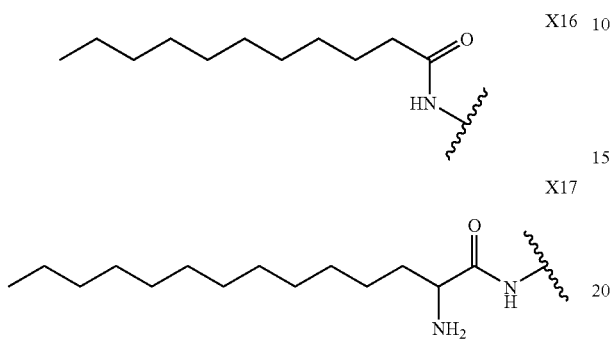
X17 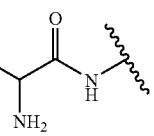
X18 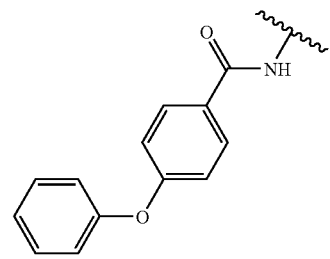
X19 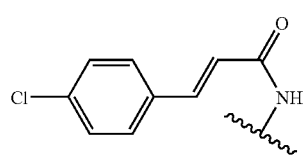
X20 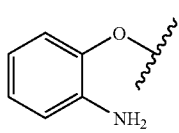
X21 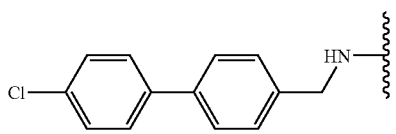
X22 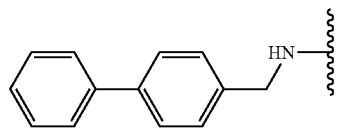
X23 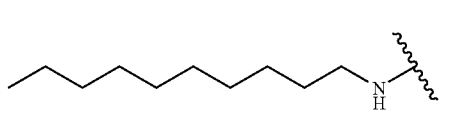
X24 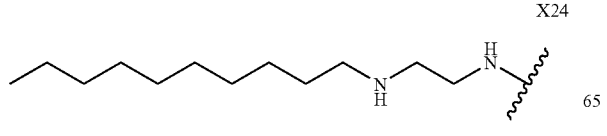
-continued
X25 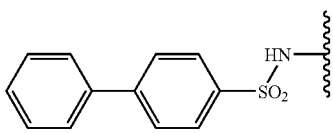
X26 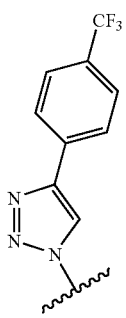
X27 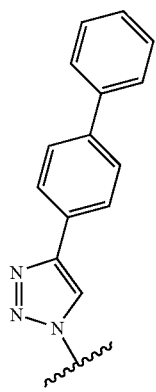
X28 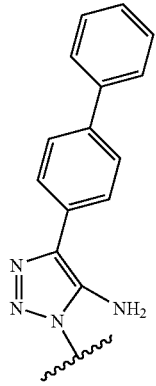
X29 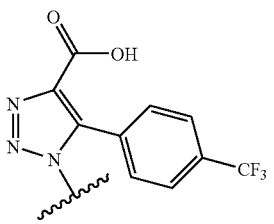

33
-continued
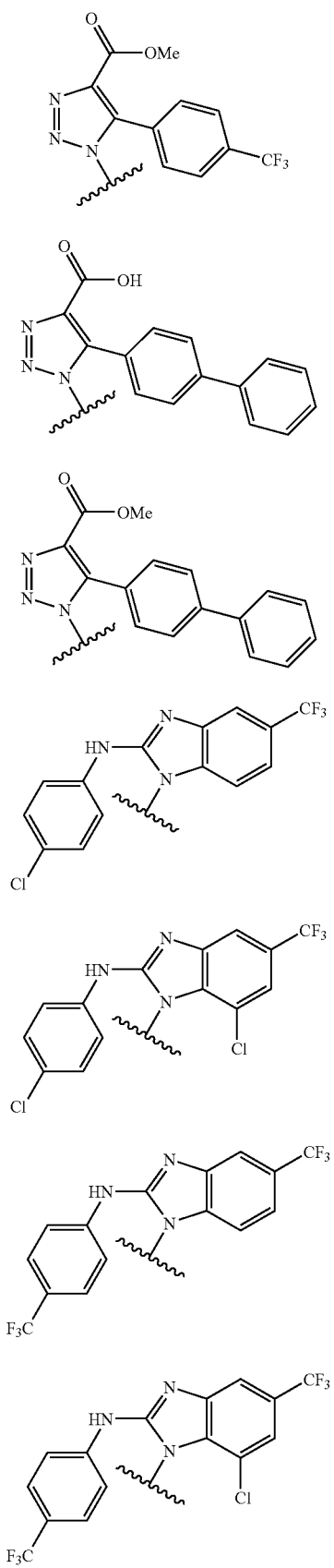
34
-continued
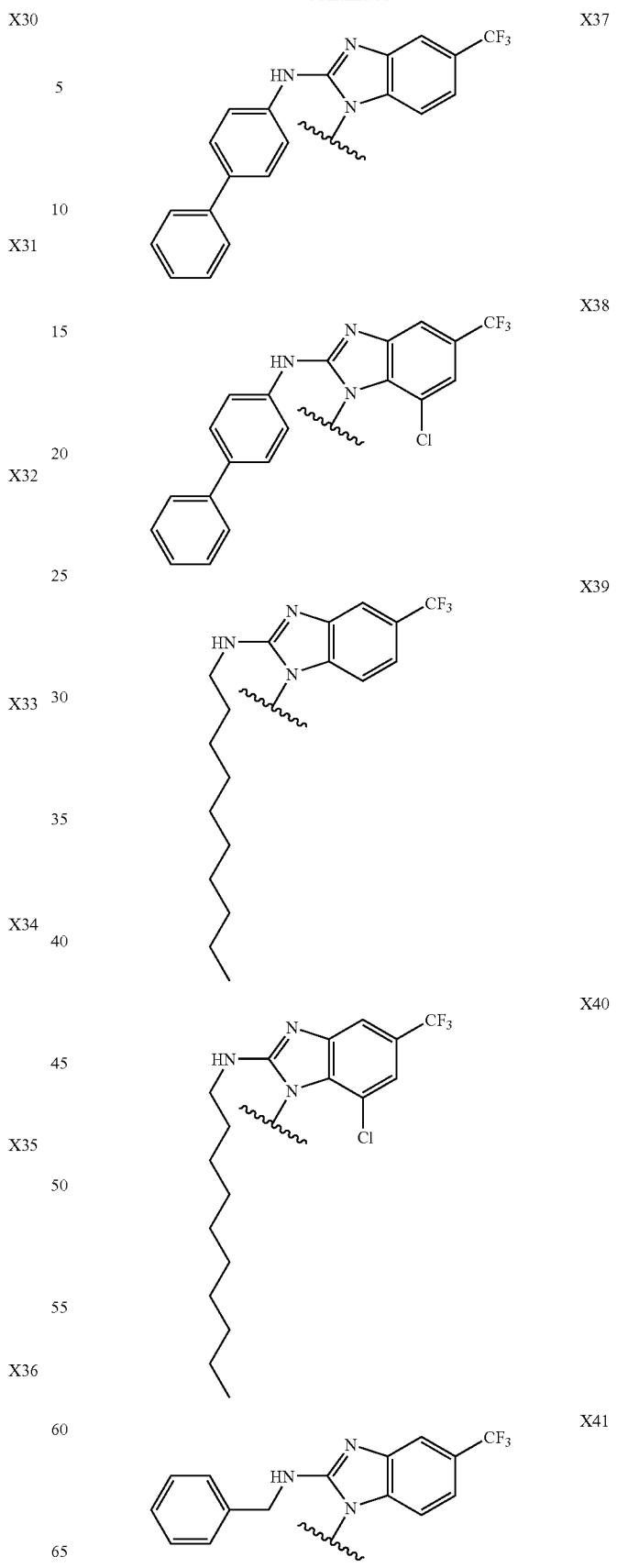

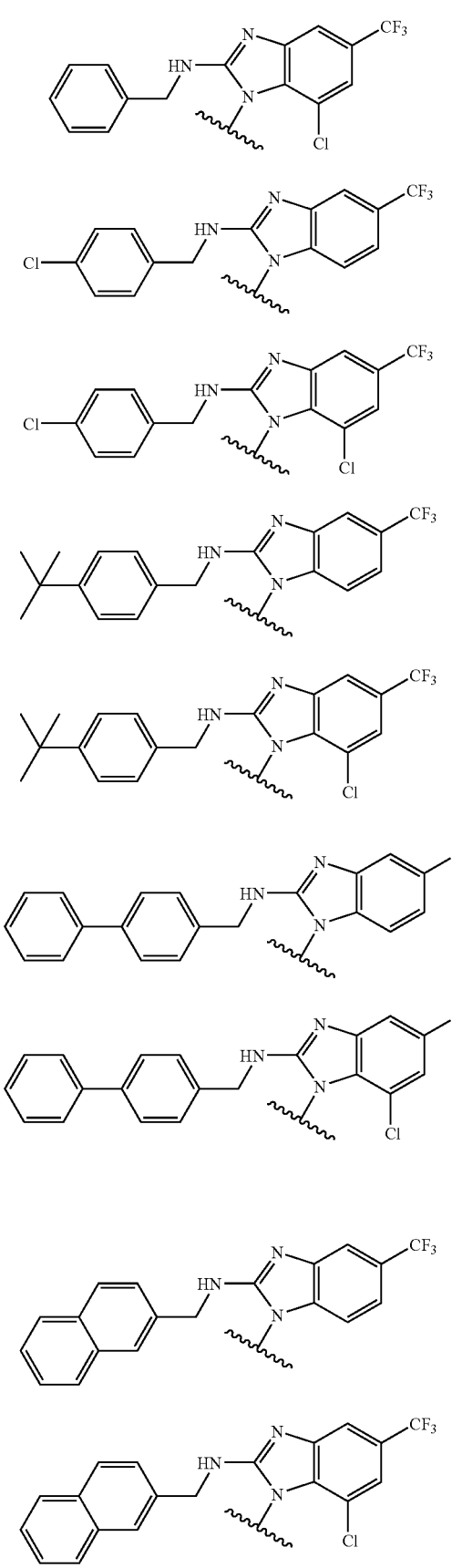
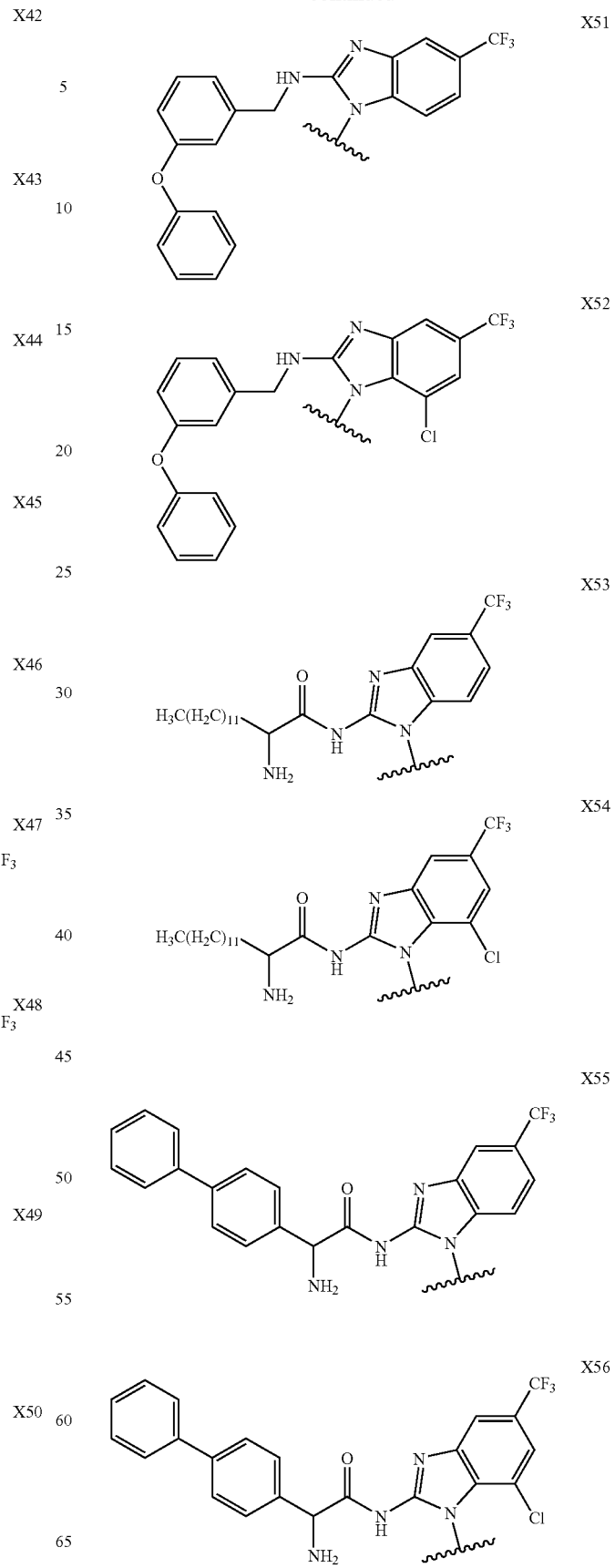

X57
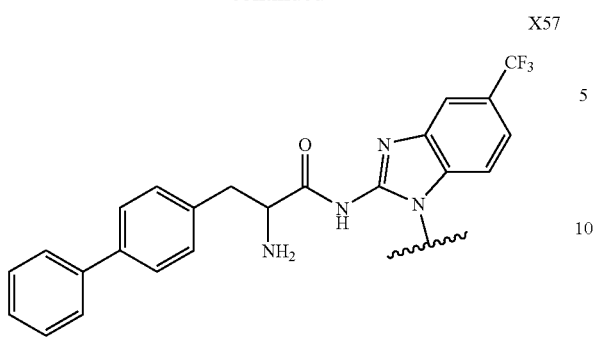
X58
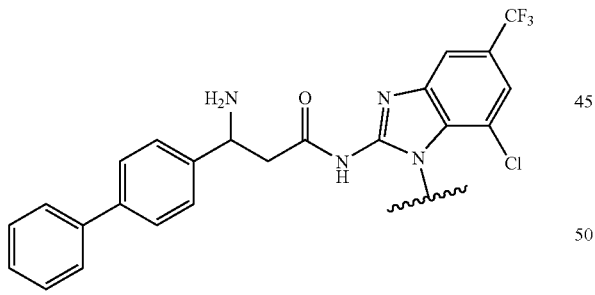
X59
X60
X61
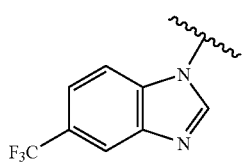
X62
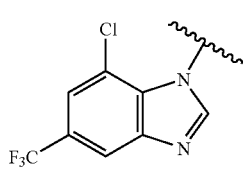
X63
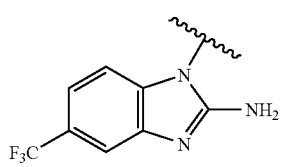
X64
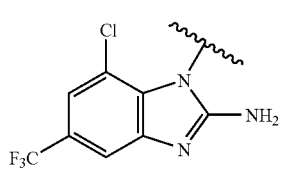
X65
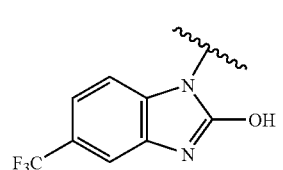
X66
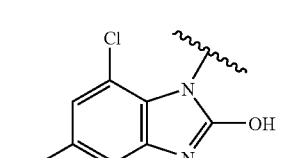
X67
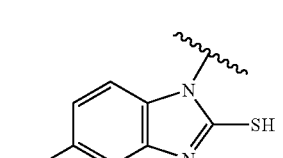
X68
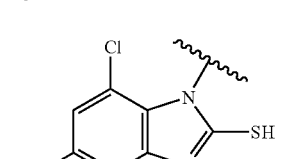
X69
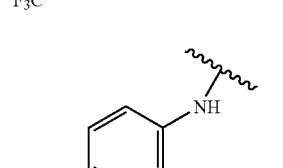
X70
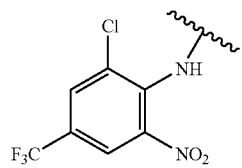
X71
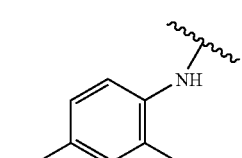

-continued

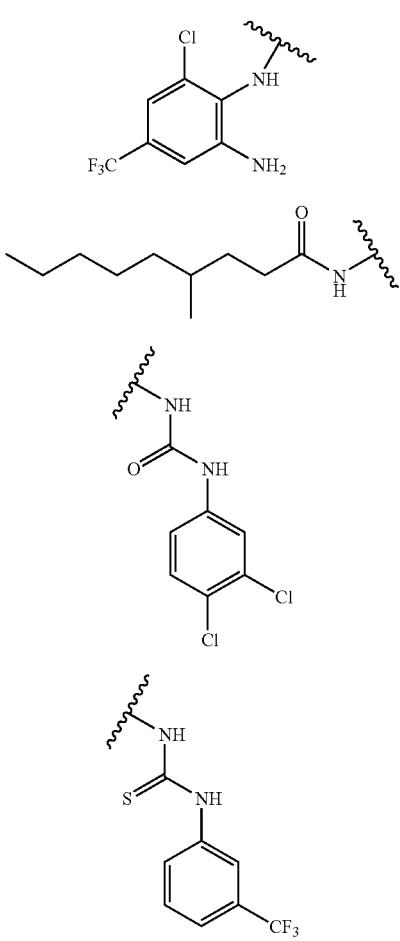

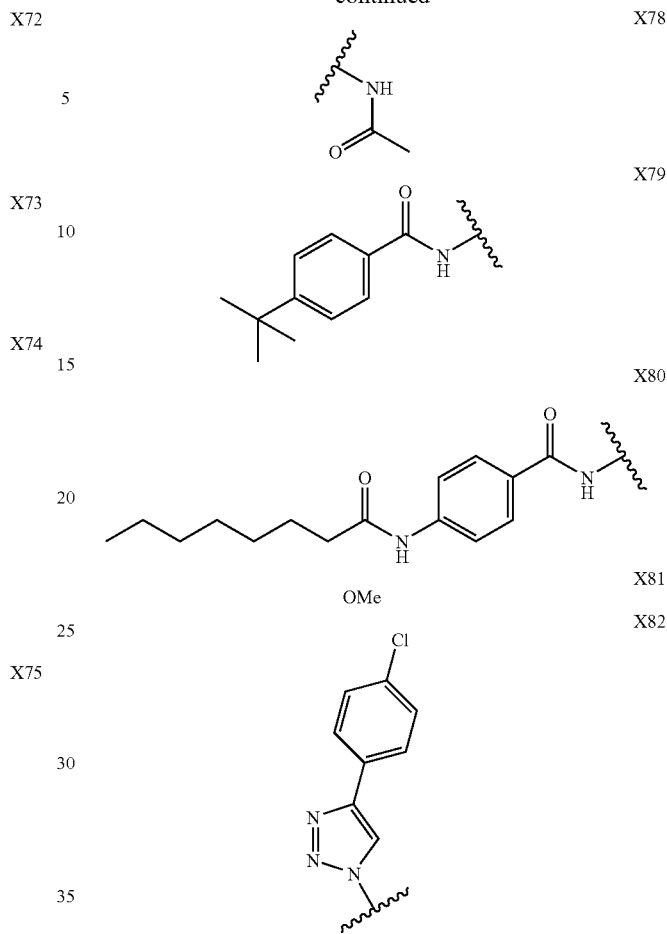

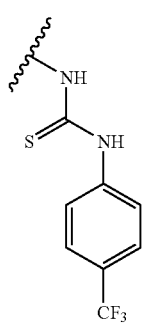

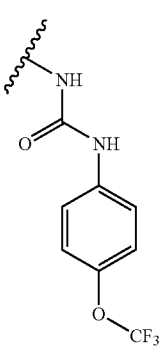

It should be appreciated that various other changes and modifications can be made to the specification without departing from the spirit and scope of the invention.

The invention claimed is:

1. A method of inhibiting bacterial growth comprising contacting bacteria with at least one monosaccharide compound, or a pharmaceutically acceptable salt thereof, of formula (1):

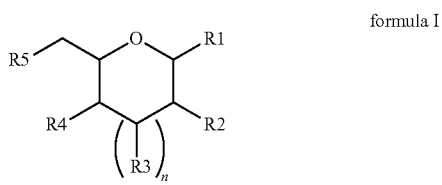

wherein, n is 1; the ring is of the galacto-configuration and the anomeric center may be of either the α or β configuration;

R1 is selected from the group consisting of hydrogen; OZ; SZ; OPO$_2$(OZ)Z; SO$_2$N(Z)Q; S(=O)N(Z)Q; N-Het wherein N and Het combine to form a heterocycle which may be further substituted with U groups; and —N(Z)Y wherein:

Y is selected from hydrogen, or the following, where G denotes the point of connection to the nitrogen atom in N(Y)Z;

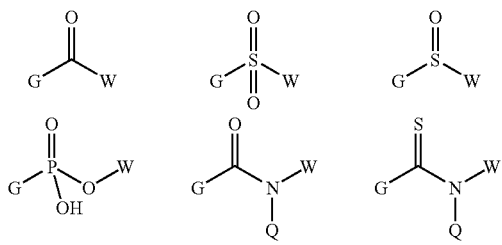

Q is selected from hydrogen or W;

the groups W are independently selected from alkyl, alkenyl, alkynyl, heteroalkyl, aryl, heteroaryl, arylalkyl and heteroarylalkyl, of 1 to 20 carbon atoms, each of which is optionally substituted, branched and/or linear; wherein W is optionally substituted by one or more substituents selected from the group consisting of OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, and hydroxamic acid;

each occurrence of Z is independently selected from the group consisting of: hydrogen, alkyl, alkenyl, alkynyl, heteroalkyl, acyl, arylacyl, heteroarylacyl, aryl, heteroaryl, arylalkyl and heteroarylalkyl, of 1 to 20 carbon atoms, each of which is optionally substituted, branched and/or linear; wherein Z is optionally substituted by one or more substituents selected from the group consisting of OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, and hydroxamic acid; or wherein each occurrence of U is independently selected from the group consisting of: OH, NO, $NO_2$, $NH_2$, $N_3$, halogen, $CF_3$, $CHF_2$, $CH_2F$, nitrile, alkoxy, aryloxy, amidine, guanidinium, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid; heteroaryloxy, aminoaryl, aminoheteroaryl, thioalkyl, thioaryl, thioheteroaryl, alkyl, alkenyl, alkynyl, acyl, arylacyl, and heteroarylacyl; of 1 to 20 carbon atoms, each of which is optionally substituted, branched and/or linear; and wherein the groups R2, R3, and R5 are independently selected from OZ or N-Het, wherein N and Het combine to form a heterocycle which may be further substituted with U groups; or N(Z)Y or $OPO_2(OZ)Z$, wherein the groups Z and Y are as defined above; and wherein R4 is N-Het, wherein N and Het combine to form a heterocycle which may be further substituted with U groups.

2. The method according to claim 1, wherein R2 is N(Z)Y.

3. The method according to claim 2 wherein the N-het heterocycle is a monocyclic or bicyclic ring of 4 to 10 membered ring structure.

4. The method according to claim 1, wherein R2 is N-Het, and wherein the N-het heterocycle is a monocyclic or bicyclic ring of 4 to 10 membered ring structure.

5. The method according to claim 1, wherein the N-het heterocyclic ring is selected from the group consisting of triazoles, benzimidazoles, benzimidazolothione, benzimidazolone, imidazole, hydanthione, thiohydanthione and purine.

6. The method according to claim 1, wherein the N-het heterocyclic ring is further substituted with U groups selected from the group consisting of substituted alkyl, aryl, carboxyl and amino.

7. The method according to claim 1, wherein the U group is selected from the group consisting of OH, NO, $NO_2$, $NH_2$, $N_3$, halogen, $CF_3$, $CHF_2$, $CH_2F$, nitrile, alkoxy, aryloxy, amidine, guanidinium, carboxylic acid, carboxylic acid ester, carboxylic acid amide, aryl, cycloalkyl, heteroalkyl, heteroaryl, primary, secondary or tertiary amines, aminoacyl, carbonyl and substituted or unsubstituted imine.

8. The method according to claim 1, wherein in each occurrence Z is independently selected from the group consisting of: hydrogen, alkyl, alkenyl, alkynyl, heteroalkyl, acyl, arylacyl, heteroarylacyl, aryl, heteroaryl, arylalkyl and heteroarylalkyl, of 1 to 20 carbon atoms which is optionally substituted, branched and/or linear.

9. The method according to claim 1, wherein the substituents are selected from the group consisting of OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, and hydroxamic acid.

10. The method according to claim 1, wherein the compound of formula I is selected from the group consisting of:

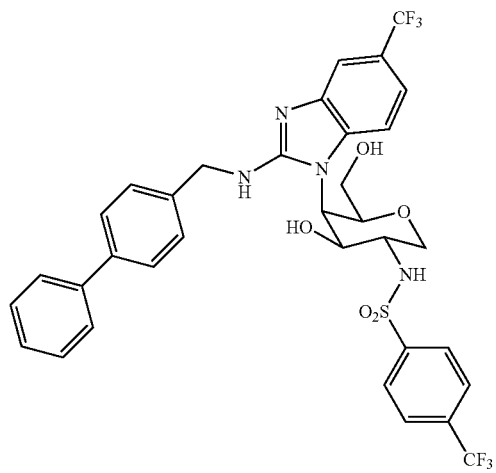

-continued

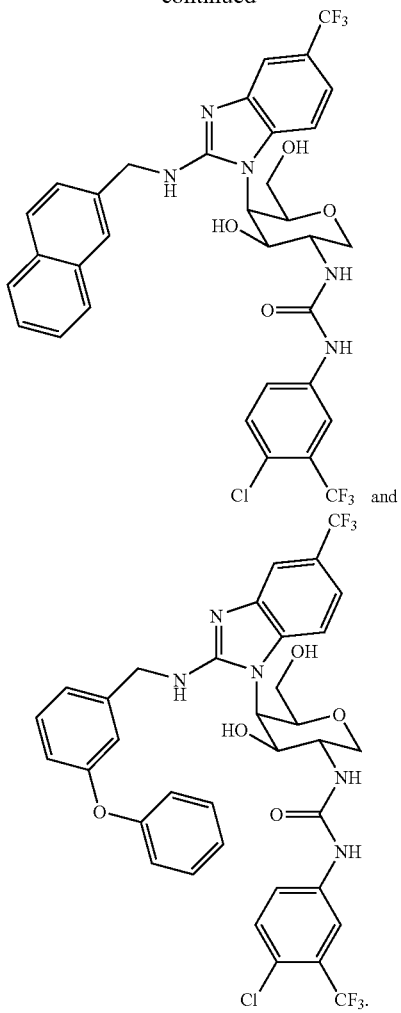

or a pharmaceutically acceptable salt thereof.

11. A pharmaceutical composition comprising a compound of formula (1) selected from the group consisting of

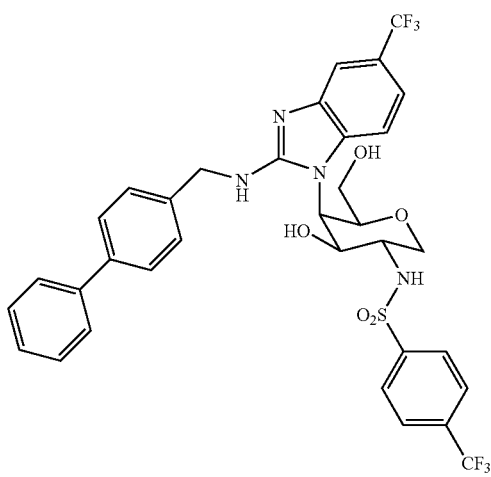

-continued

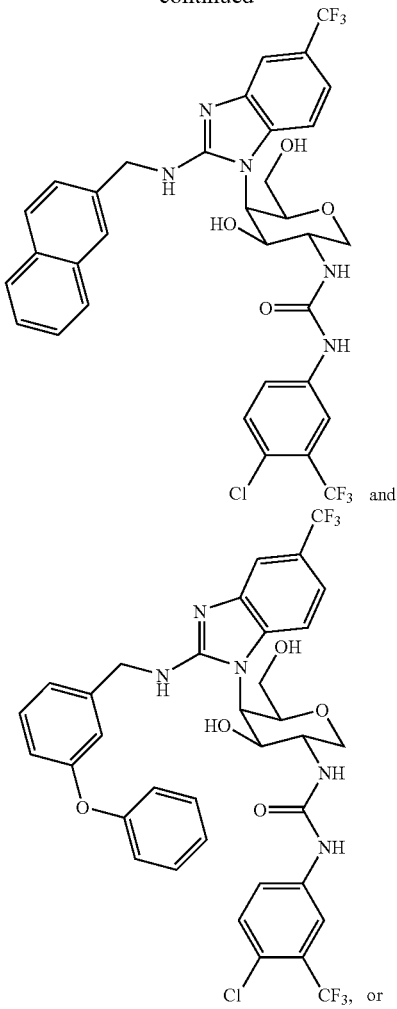

tautomers, esters, solvates, or pharmaceutically acceptable salts thereof, and a pharmaceutically acceptable carrier.

12. The method of claim 1, wherein the bacteria is Gram-positive bacteria.

13. The method of claim 1, wherein the bacteria is selected from the group consisting of an *Escherichia* bacteria, a *Staphylococcus* bacteria, *Micrococcus* bacteria, an *Enterococcus* bacteria, and a *Streptococcus* bacteria.

14. The method of claim 1, wherein said contacting comprises administering an effective amount of a compound of formula (1), or a pharmaceutically acceptable salt thereof, to a subject in need of such treatment.

15. The method of claim 13, wherein the *Staphylococcus* bacteria is a methicillin resistant Staphylococci.

16. The method of claim 13, wherein the *Staphylococcus* bacteria is selected from the group consisting of *Staphylococcus* aureus and *Staphylococcus* aureus MRSA.

17. The method of claim 13, wherein the *Enterococcus* bacteria is a Vancomycin resistant *Enterococci*.

18. The method of claim 2, wherein R1 is hydrogen.

* * * * *